US008541366B2

(12) United States Patent
Carozzi et al.

(10) Patent No.: US 8,541,366 B2
(45) Date of Patent: Sep. 24, 2013

(54) SYNTHETIC AXMI-004 DELTA-ENDOTOXIN GENES AND METHODS FOR THEIR USE

(75) Inventors: Nadine Carozzi, Raleigh, NC (US);
Nalini Desai, Chapel Hill, NC (US);
Daniel J. Tomso, Bahama, NC (US);
Vadim Beilinson, Cary, NC (US);
Theodore Kahn, Cary, NC (US)

(73) Assignee: Athenix Corporation, Morrisville, NC (US)

( * ) Notice: Subject to any disclaimer, the term of this patent is extended or adjusted under 35 U.S.C. 154(b) by 763 days.

(21) Appl. No.: 12/209,354

(22) Filed: Sep. 12, 2008

(65) Prior Publication Data

US 2009/0099081 A1  Apr. 16, 2009

Related U.S. Application Data

(60) Provisional application No. 60/972,546, filed on Sep. 14, 2007.

(51) Int. Cl.
*A01N 37/18* (2006.01)
*C07K 14/325* (2006.01)

(52) U.S. Cl.
USPC ........................................................ 514/4.5

(58) Field of Classification Search
None
See application file for complete search history.

(56) References Cited

U.S. PATENT DOCUMENTS

| | | | |
|---|---|---|---|
| 5,380,831 A | 1/1995 | Adang et al. | |
| 5,866,784 A | 2/1999 | Van Mellaert et al. | |
| 5,908,970 A | 6/1999 | Van Mellaert et al. | |
| 6,172,281 B1 | 1/2001 | Van Mellaert et al. | |
| 6,177,615 B1 | 1/2001 | Baum | |
| 6,833,449 B1 | 12/2004 | Barton et al. | |
| 7,355,099 B2 * | 4/2008 | Carozzi et al. ............... | 800/302 |
| 2001/0003849 A1 | 6/2001 | Barton | |
| 2004/0197916 A1* | 10/2004 | Carozzi et al. ............... | 435/468 |
| 2008/0040827 A1 | 2/2008 | Donovan et al. | |
| 2008/0172764 A1 | 7/2008 | Carozzi et al. | |
| 2008/0176801 A1 | 7/2008 | Carozzi et al. | |

FOREIGN PATENT DOCUMENTS

| | | | |
|---|---|---|---|
| WO | WO 2004/074462 A2 | 9/2004 | |
| WO | WO 2005/107383 | * | 11/2005 |
| WO | WO 2005/107383 A2 | 11/2005 | |

OTHER PUBLICATIONS de Maagd et al, 1999, Appl. Environ. Microbiol. 65:4369-4374.*
Tounsi et al, 2003, J. Appl. Microbiol. 95:23-28.*
Aaronson et al (2001, FEMS Microbiol. Lett. 195:1-8).*
de Maagd et al (2001, Trends Genet. 17:193-199).*
Guo et al (2004, Proc. Natl. Acad. Sci. USA 101: 9205-9210).*
Partial International Search Report, Annex to Form PCT/ISA, 206, issued Dec. 12, 2008 for PCT/US/2008/076104.

Angsuthanasombat, C., et al., "Directed Mutagenesis of the *Bacillus thuringiensis* Cry11A Toxin Reveals a Crucial Role in Larvicidal Activity of Arginine-136 in Helix 4," *J. Biochem. Mol. Biol.*, Sep. 2001, pp. 402-407, vol. 34, No. 5.
Aronson, A.I., and Shai, Y., "Why *Bacillus thuringiensis* Insecticidal Toxins are so Effective: Unique Features of Their Mode of Action," *FEMS Microbiology Letters*, 2001, pp. 1-8.
De Maagd, R.A., et al., "Identification of *Bacillus thuringiensis* Delta-Endotoxin Cry1C Domain III Amino Acid Residues Involved in Insect Specificity," *Appl. Environ. Microbiol.*, Oct. 1999, pp. 4369-4374, vol. 65, No. 10.
De Maagd, R.A., et al., "How *Bacillus thuringiensis* has Evolved Specific Toxins to Colonize the Insect World," Trends Genet., Apr. 2001, pp. 193-199, vol. 17, No. 4.
Guo, H.H., et al., "Protein Tolerance to Random Amino Acid Change," *PNAS*, Jun. 22, 2004, pp. 9205-9210, vol. 101, No. 25.
Hill, M.A. and Preiss, J., "Functional Analysis of Conserved Histidines in ADP-Glucose Pyrophosphorylase from *Escherichia coli*," *Biochem. Biophys. Res. Comm.*, Mar. 1998, pp. 573-577, vol. 244.
Honée, G., et al., "Nucleotide Sequence of Crystal Protein Gene Isolated from *B. thuringiensis* subspecies *entomocidus* 60.5 Coding for a Toxin Highly Active Against *Spodoptera* Species," *Nucleic Acids Research*, May 13, 1988, p. 6240, vol. 16, No. 13.
Jenkins, J.L., et al., "Binding of *Bacillus thuringiensis* Cry1Ac Toxin to *Manduca sexta* Aminopeptidase-N Receptor is Not Directly Related to Toxicity," *FEBS Letters*, 1999, pp. 373-376, vol. 462.
Kalman, et al., "Cloning of a Novel *cryIC*-type Gene from a Strain of *Bacillus thuringiensis* subsp. *galleriae*," *Applied and Environmental Microbiology*, 1993, pp. 1131-1137, vol. 59, No. 4.
Lazar, E., et al., "Transforming Growth Factor α: Mutation of Aspartic Acid 47 and Leucine 48 Results in Different Biological Activities," *Mol. Cell. Biol.*, Mar. 1988, pp. 1247-1252, vol. 8, No. 3.
Lee, M.K., et al., "Mutations at the Argine Residues in α8 Loop of *Bacillus thuringiensis* δ-endotoxin Cry1Ac Affect Toxicity and Binding to *Manduca sexta* and *Lymantria dispar* Aminopeptidase N," *FEBS Letters*, 2001, pp. 108-112, vol. 497.
Masson, L., et al., "Mutagenic Analysis of a Conserved Region of Domain III in the Cry1Ac Toxin of *Bacillus thuringiensis*," *Appl. Environ. Microbiol.*, Jan. 2002, pp. 194-200, vol. 68, No. 1.
Rajamohan, F., et al., "Mutations at Domain II, Loop 3, of *Bacillus thuringiensis* Cry1Aa and Cry1Ab δ-Endotoxins Suggest Loop 3 is Involved in Initial Binding to Lepidopteran Midguts," *J. Biol. Chem.*, Oct. 11, 1996, pp. 25220-25226, vol. 271, No. 41.
Sanchis, V., et al., "Nucleotide Sequence and Analysis of the N—terminal Coding Region of the Spodoptera-active δ-endotoxin Gene of *Bacillus thuringiensis aizawai* 7.29," *Mol. Microbiol.*, 1989, pp. 229-238, vol. 3, No. 2.

(Continued)

*Primary Examiner* — Anne Kubelik

(57) ABSTRACT

Compositions and methods for conferring pesticidal activity to bacteria, plants, plant cells, tissues and seeds are provided. Compositions comprising a coding sequence for a delta-endotoxin polypeptide are provided, particularly synthetically-derived coding sequences. The coding sequences can be used in DNA constructs or expression cassettes for transformation and expression in plants and bacteria. Compositions also comprise transformed bacteria, plants, plant cells, tissues, and seeds. In particular, isolated delta-endotoxin nucleic acid molecules are provided. Additionally, amino acid sequences corresponding to the polynucleotides are encompassed, and antibodies specifically binding to those amino acid sequences. In particular, the present invention provides for isolated nucleic acid molecules comprising nucleotide sequences encoding the amino acid sequence shown in SEQ ID NO:9, 11, 13, 15, or 18, or the nucleotide sequence set forth in SEQ ID NO:1, 2, 4, 6, 7, 8, 10, 12, 14, 16, or 17, as well as variants and fragments thereof.

8 Claims, 2 Drawing Sheets

(56) References Cited

OTHER PUBLICATIONS

Schwartz, J.L., et al., "Single-Site Mutations in the Conserved Alternating-Arginine Region Affect Ionic Channels Formed by Cry1Aa, a *Bacillus thuringiensis* Toxin," *Appl. Environ. Microbiol.*, Oct. 1997, pp. 3978-3984, vol. 63, No. 10.

Tounsi, S., et al., "Cloning and Study of the Expression of a Novel cry1 *1a*-type Gene from *Bacillus thuringiensis subsp. Kurstaki*," *J Appl. Microbiol.* 2003, pp. 23-28, vol. 95.

NCBI Database Report for Accession No. AAA22343, 1991.

NCBI Database Report for Accession No. AAF37224, Direct Submission on Dec. 14, 1999.

NCBI Database Report for Accession No. AAM00264, Direct Submission on Mar. 16, 2001.

NCBI Database Report for Accession No. AAN16462, Direct Submission on Aug. 22, 2002.

NCBI Database Report for Accession No. CAA65457, Direct Submission on Mar. 18, 1996.

* cited by examiner

```
004           MSELKGKFKKSTNRTCCLLKIINIGGRGMNSKEHDYLKVCNDLSDANINMERFDKNDALE 60
004B_2M       ------------------------------MNSKEHDYLKVCNDLSDANINMERFDKNDALE 32
004B_3M       -------------------------------------------------MERFDKNDALE 11
004B_3M_ALT1  -------------------------MKVTIQPGDLTGIIQSPASKSSMERFDKNDALE 33
004B_3M_ALT2  ----------------------------------------------MAAMERFDKNDALE 14
004B_3M_ALT3  ----------------------------------------------MQIMERFDKNDALE 14
                                                               **********

004           IGMSIVSELIGMIPGGTALQFVFNQLWSRLGDSGWNAFMEHVEELIDTKIEGYAKNKALS 120
004B_2M       IGMSIVSELIGMIPGGTALQFVFNQLWSRLGDSGWNAFMEHVEELIDTKIEGYAKNKALS 92
004B_3M       IGMSIVSELIGMIPGGTALQFVFNQLWSRLGDSGWNAFMEHVEELIDTKIEGYAKNKALS 71
004B_3M_ALT1  IGMSIVSELIGMIPGGTALQFVFNQLWSRLGDSGWNAFMEHVEELIDTKIEGYAKNKALS 93
004B_3M_ALT2  IGMSIVSELIGMIPGGTALQFVFNQLWSRLGDSGWNAFMEHVEELIDTKIEGYAKNKALS 74
004B_3M_ALT3  IGMSIVSELIGMIPGGTALQFVFNQLWSRLGDSGWNAFMEHVEELIDTKIEGYAKNKALS 74
              ************************************************************

004           ELAGIQRNLETYIQLRNEWENDIENSKAQGKVANYYESLEQAVERSMPQFAVENFEVPLL 180
004B_2M       ELAGIQRNLETYIQLRNEWENDIENSKAQGKVANYYESLEQAVERSMPQFAVENFEVPLL 152
004B_3M       ELAGIQRNLETYIQLRNEWENDIENSKAQGKVANYYESLEQAVERSMPQFAVENFEVPLL 131
004B_3M_ALT1  ELAGIQRNLETYIQLRNEWENDIENSKAQGKVANYYESLEQAVERSMPQFAVENFEVPLL 153
004B_3M_ALT2  ELAGIQRNLETYIQLRNEWENDIENSKAQGKVANYYESLEQAVERSMPQFAVENFEVPLL 134
004B_3M_ALT3  ELAGIQRNLETYIQLRNEWENDIENSKAQGKVANYYESLEQAVERSMPQFAVENFEVPLL 134
              ************************************************************

004           TVYVQAANLHLLLLRDVSVYGKCWGWSEQKIKIYYDKQIKYTHEYTNHCVNWYNKGLERL 240
004B_2M       TVYVQAANLHLLLLRDVSVYGKCWGWSEQKIKIYYDKQIKYTHEYTNHCVNWYNKGLERL 212
004B_3M       TVYVQAANLHLLLLRDVSVYGKCWGWSEQKIKIYYDKQIKYTHEYTNHCVNWYNKGLERL 191
004B_3M_ALT1  TVYVQAANLHLLLLRDVSVYGKCWGWSEQKIKIYYDKQIKYTHEYTNHCVNWYNKGLERL 213
004B_3M_ALT2  TVYVQAANLHLLLLRDVSVYGKCWGWSEQKIKIYYDKQIKYTHEYTNHCVNWYNKGLERL 194
004B_3M_ALT3  TVYVQAANLHLLLLRDVSVYGKCWGWSEQKIKIYYDKQIKYTHEYTNHCVNWYNKGLERL 194
              ************************************************************

004           KNKGSSYQDWYNYNRFRREMTLTVLDIVALFPHYDVQTYPITTVAQLTREVYTDPLLNFN 300
004B_2M       KNKGSSYQDWYNYNRFRREMTLTVLDIVALFPHYDVQTYPITTVAQLTREVYTDPLLNFN 272
004B_3M       KNKGSSYQDWYNYNRFRREMTLTVLDIVALFPHYDVQTYPITTVAQLTREVYTDPLLNFN 251
004B_3M_ALT1  KNKGSSYQDWYNYNRFRREMTLTVLDIVALFPHYDVQTYPITTVAQLTREVYTDPLLNFN 273
004B_3M_ALT2  KNKGSSYQDWYNYNRFRREMTLTVLDIVALFPHYDVQTYPITTVAQLTREVYTDPLLNFN 254
004B_3M_ALT3  KNKGSSYQDWYNYNRFRREMTLTVLDIVALFPHYDVQTYPITTVAQLTREVYTDPLLNFN 254
              ************************************************************

004           PKLHSVSQLPSFSDMENATIRTPHLMEFLRMLTIYTDWYSVGRNYYWGGHRVTSYHVGGE 360
004B_2M       PKLHSVSQLPSFSDMENATIRTPHLMEFLRMLTIYTDWYSVGRNYYWGGHRVTSYHVGGE 332
004B_3M       PKLHSVSQLPSFSDMENATIRTPHLMEFLRMLTIYTDWYSVGRNYYWGGHRVTSYHVGGE 311
004B_3M_ALT1  PKLHSVSQLPSFSDMENATIRTPHLMEFLRMLTIYTDWYSVGRNYYWGGHRVTSYHVGGE 333
004B_3M_ALT2  PKLHSVSQLPSFSDMENATIRTPHLMEFLRMLTIYTDWYSVGRNYYWGGHRVTSYHVGGE 314
004B_3M_ALT3  PKLHSVSQLPSFSDMENATIRTPHLMEFLRMLTIYTDWYSVGRNYYWGGHRVTSYHVGGE 314
              ************************************************************
```

FIG. 1A

```
004            NIRSPLYGREANQEVPRDFYFYGPVFKTLSKPTLRPLQQPAPAPPFNLRSLEGVEFHTPT  420
004B_2M        NIRSPLYGREANQEVPRDFYFYGPVFKTLSKPTLRPLQQPAPAPPFNLRSLEGVEFHTPT  392
004B_3M        NIRSPLYGREANQEVPRDFYFYGPVFKTLSKPTLRPLQQPAPAPPFNLRSLEGVEFHTPT  371
004B_3M_ALT1   NIRSPLYGREANQEVPRDFYFYGPVFKTLSKPTLRPLQQPAPAPPFNLRSLEGVEFHTPT  393
004B_3M_ALT2   NIRSPLYGREANQEVPRDFYFYGPVFKTLSKPTLRPLQQPAPAPPFNLRSLEGVEFHTPT  374
004B_3M_ALT3   NIRSPLYGREANQEVPRDFYFYGPVFKTLSKPTLRPLQQPAPAPPFNLRSLEGVEFHTPT  374
               ************************************************************

004            GSFMYRERGSVDSFNELPPFNPVGLPHKVYSHRLCHATFVRKSGTPYLTTGAIFSWTHRS  480
004B_2M        GSFMYRERGSVDSFNELPPFNPVGLPHKVYSHRLCHATFVRKSGTPYLTTGAIFSWTHRS  452
004B_3M        GSFMYRERGSVDSFNELPPFNPVGLPHKVYSHRLCHATFVRKSGTPYLTTGAIFSWTHRS  431
004B_3M_ALT1   GSFMYRERGSVDSFNELPPFNPVGLPHKVYSHRLCHATFVRKSGTPYLTTGAIFSWTHRS  453
004B_3M_ALT2   GSFMYRERGSVDSFNELPPFNPVGLPHKVYSHRLCHATFVRKSGTPYLTTGAIFSWTHRS  434
004B_3M_ALT3   GSFMYRERGSVDSFNELPPFNPVGLPHKVYSHRLCHATFVRKSGTPYLTTGAIFSWTHRS  434
               ************************************************************

004            AEETNTIESNIITQIPLVKAYQIGSGTTVRKGPGFTGGDILRRTGPGTFGDMRININAPL  540
004B_2M        AEETNTIESNIITQIPLVKAYQIGSGTTVRKGPGFTGGDILRRTGPGTFGDMRININAPL  512
004B_3M        AEETNTIESNIITQIPLVKAYQIGSGTTVRKGPGFTGGDILRRTGPGTFGDMRININAPL  491
004B_3M_ALT1   AEETNTIESNIITQIPLVKAYQIGSGTTVRKGPGFTGGDILRRTGPGTFGDMRININAPL  513
004B_3M_ALT2   AEETNTIESNIITQIPLVKAYQIGSGTTVRKGPGFTGGDILRRTGPGTFGDMRININAPL  494
004B_3M_ALT3   AEETNTIESNIITQIPLVKAYQIGSGTTVRKGPGFTGGDILRRTGPGTFGDMRININAPL  494
               ************************************************************

004            SQRYRVRIRYASTTDLQFVTSINGTTINIGNFPKTINNLNTLGSEGYRTVSFSTPFSFSN  600
004B_2M        SQRYRVRIRYASTTDLQFVTSINGTTINIGNFPKTINNLNTLGSEGYRTVSFSTPFSFSN  572
004B_3M        SQRYRVRIRYASTTDLQFVTSINGTTINIGNFPKTINNLNTLGSEGYRTVSFSTPFSFSN  551
004B_3M_ALT1   SQRYRVRIRYASTTDLQFVTSINGTTINIGNFPKTINNLNTLGSEGYRTVSFSTPFSFSN  573
004B_3M_ALT2   SQRYRVRIRYASTTDLQFVTSINGTTINIGNFPKTINNLNTLGSEGYRTVSFSTPFSFSN  554
004B_3M_ALT3   SQRYRVRIRYASTTDLQFVTSINGTTINIGNFPKTINNLNTLGSEGYRTVSFSTPFSFSN  554
               ************************************************************

004            AQSIFRLGIQAFSGVQEVYVDKIEFIPVE  629
004B_2M        AQSIFRLGIQAFSGVQEVYVDKIEFIPVE  601
004B_3M        AQSIFRLGIQAFSGVQEVYVDKIEFIPVE  580
004B_3M_ALT1   AQSIFRLGIQAFSGVQEVYVDKIEFIPVE  602
004B_3M_ALT2   AQSIFRLGIQAFSGVQEVYVDKIEFIPVE  583
004B_3M_ALT3   AQSIFRLGIQAFSGVQEVYVDKIEFIPVE  583
               *****************************
```

FIG. 1B

```
SEQUENCE LISTING

<160> NUMBER OF SEQ ID NOS: 18

<210> SEQ ID NO 1
<211> LENGTH: 1890
<212> TYPE: DNA
<213> ORGANISM: Artificial Sequence
<220> FEATURE:
<223> OTHER INFORMATION: synthetic nucleotide sequence encoding AXMI-004
      (synaxmi-004)

<400> SEQUENCE: 1
atgagcgaac tgaagggcaa gttcaagaag tccaccaacc gcacgtgctg cctcctgaag      60
atcatcaaca tcggggggcag aggtatgaac agcaaggaac atgattacct caaggtttgc     120
aacgatctgt ccgatgcaaa catcaacatg gaacggttcg ataagaacga tgcactcgaa     180
```

```
atcggcatgt caatcgtgtc cgaactgatc gggatgatcc caggcgggac cgctcttcag    240
ttcgtgttca accagctttg gagccgtctc ggcgattccg gctggaacgc attcatggaa    300
catgtggaag aactgatcga tacgaagatc gaagggtacg caaagaacaa ggcactctca    360
gaacttgcag gcatccagag aaacctcgaa acctacatcc agctgcgtaa cgaatgggaa    420
aacgatatcg aaaactccaa ggctcagggg aaggtggcta actactacga aagcctcgaa    480
caggcagttg aaagatccat gcctcagttc gcagtggaaa acttcgaagt gccacttctc    540
acggtgtacg tgcaggctgc taaccttcat ctcctgctcc tgagagatgt ttcagtttac    600
ggcaagtgct gggggtggtc cgaacagaag atcaagatct actacgataa gcagatcaag    660
tacacccatg aatacacgaa ccattgcgtg aactggtaca acaagggcct tgaaagactc    720
aagaacaagg ggagctcata ccaggattgg tacaactaca accgtttccg tagagaaatg    780
actctgaccg ttctcgatat cgttgctctg ttcccacatt acgatgtgca gacctaccca    840
atcacgaccg ttgctcagct caccagagaa gtttacacgg accctcttct gaacttcaac    900
cctaagctgc attcagtgtc ccagctccct agcttctccg atatggaaaa cgcaaccatc    960
agaacgccac atctgatgga gttcctcaga atgctgacca tctacacgga ttggtacagc   1020
gtggggagaa actactactg ggcgggcat cgcgtgacct cctaccatgt gggcggggaa   1080
aacatcagat cacctctcta cggcagagaa gcaaaccaag aagttcctag agatttctac   1140
ttctacggcc cagttttcaa gacgctgtcc aagcctaccc ttcgtccact ccagcagcct   1200
gcaccagctc ctcctttcaa cctgagaagc ctcgaagggg tggagttcca tacccctacg   1260
ggctcattca tgtaccgtga aagagggagc gtggattcct tcaacgaact tccacctttc   1320
aacccagttg gcctccctca taaggtgtac agccatcgtc tgtgccatgc aacattcgtt   1380
cgtaagtccg ggactcctta cctgaccacg ggcgctatct tcagctggac ccatcgttcc   1440
gctgaagaaa cgaacaccat cgaatcaaac atcatcacgc agatcccact ggtgaaggca   1500
taccagatcg gtagcggcac cacggtgaga aaggggccag gcttcacggg gggcgatatc   1560
cttcgcagaa ccggccctgg gacgttcggc gatatgagaa tcaacatcaa cgcaccactg   1620
agccaaagat accgtgtgag aatccgttac gcttcaacca cggatcttca gttcgtgacc   1680
agcatcaacg ggacgaccat caacatcggc aacttcccta agacgatcaa caacctgaac   1740
accctcggct ccgaaggcta cagaacggtg agcttctcca ccccattcag cttctccaac   1800
gcacagagca tcttcagact tggcatccag gcattctcag gcgttcagga agtttacgtg   1860
gataagatcg agttcatccc tgttgaatag                                    1890

<210> SEQ ID NO 2
<211> LENGTH: 1890
<212> TYPE: DNA
<213> ORGANISM: Artificial Sequence
<220> FEATURE:
<223> OTHER INFORMATION: synthetic nucleotide sequence encoding AXMI-004
      (synaxmi-004B)

<400> SEQUENCE: 2
atgagcgagc tcaagggtaa gttcaagaag tccaccaacc gcacctgctg cctcctcaag     60
atcatcaata tcggtggccg cggcatgaac tcaaaggagc atgattacct caaggtctgc    120
aacgatctct ccgatgccaa catcaacatg gagcgcttcg ataagaacga tgccctcgag    180
atcggcatgt ccatcgtctc cgagctcatc ggcatgatcc ccggcggcac cgccctgcag    240
ttcgtcttca accagctctg gagccgcctc ggcgactcag gctggaacgc tttcatggag    300
```

```
catgtcgagg agctcatcga taccaagatc gagggctacg ccaagaacaa ggccctgtcc    360
gagctggccg gtatccagcg taacctggag acctacatcc agctgaggaa cgagtgggag    420
aacgatatcg agaactccaa ggcccagggc aaggtcgcta actactacga gagcctggag    480
caggccgtca gcgttcaat gcctcagttc gccgttgaga acttcgaggt ccccttgctg     540
accgtctacg tccaggctgc taacctccat ctcctgctcc tcagggatgt cagcgtttac    600
ggcaagtgct ggggttggtc tgagcagaag atcaagatct actacgataa gcagatcaag    660
tacacccatg agtacaccaa ccattgcgtc aactggtaca acaagggcct ggagcgcctg    720
aagaacaagg gctcaagcta ccaggattgg tacaactaca accgcttccg ccgcgagatg    780
accctgaccg tcctcgatat cgtcgccctg ttcccccatt acgatgtcca gacctacccc    840
atcaccaccg tcgcccagct cacccgcgag gtctacactg atcccctcct gaacttcaac    900
cccaagctcc attcagtcag ccagctgccc agcttcagcg atatggagaa cgccaccatc    960
cgcaccccc atctgatgga gttcctgcgc atgctgacca tctacaccga ttggtacagc    1020
gtcggccgca actactactg gggcggccat cgcgtcacct cataccatgt cggcggcgag    1080
aacatccgct ctcctctgta cggtagggag gctaaccagg aggtccctag ggatttctac    1140
ttctacggcc ccgtcttcaa gaccctgtcc aagcccaccc tgaggccttt gcagcagcct    1200
gctcctgctc ctcctttcaa cttgcgttct ctggagggtg ttgagttcca tacccccacc    1260
ggttcattca tgtaccgcga gcgcggttct gtcgatagct caacgagct gccccctttc     1320
aaccccgtcg gtttgcctca taaggtctac agccatcgcc tgtgccatgc caccttcgtc    1380
cgtaagagcg gcacccctta cctgaccacc ggtgctatct tctcctggac ccataggtcc    1440
gctgaggaga ctaacaccat cgagtcaaac atcatcaccc agatcccccct cgtcaaggcc    1500
taccagatcg gcagcggcac caccgtccgt aagggtcctg gtttcaccgg tggtgatatc    1560
ctcaggcgta ccggtcctgg tactttcggt gatatgagga tcaacatcaa cgccccctc     1620
tcccagaggt acagggtccg tatccgttac gcctctacca ccgatctgca gttcgtcacc    1680
tcaatcaacg gcaccaccat caacatcggc aacttcccca agaccatcaa caacctgaac    1740
accctgggct ccgagggcta ccgcaccgtc tctttctcca ccccttttcag cttctctaac    1800
gcccagtcca tcttccgcct cggtatccag gctttcagcg tgtccaggga ggtttacgtc    1860
gataagatcg agttcatccc cgtcgagtga                                     1890
```

<210> SEQ ID NO 3
<211> LENGTH: 629
<212> TYPE: PRT
<213> ORGANISM: Bacillus thuringiensis

<400> SEQUENCE: 3

Met Ser Glu Leu Lys Gly Lys Phe Lys Lys Ser Thr Asn Arg Thr Cys
1               5                   10                  15

Cys Leu Leu Lys Ile Ile Asn Ile Gly Gly Arg Gly Met Asn Ser Lys
            20                  25                  30

Glu His Asp Tyr Leu Lys Val Cys Asn Asp Leu Ser Asp Ala Asn Ile
        35                  40                  45

Asn Met Glu Arg Phe Asp Lys Asn Asp Ala Leu Glu Ile Gly Met Ser
    50                  55                  60

Ile Val Ser Glu Leu Ile Gly Met Ile Pro Gly Gly Thr Ala Leu Gln
65                  70                  75                  80

Phe Val Phe Asn Gln Leu Trp Ser Arg Leu Gly Asp Ser Gly Trp Asn
                85                  90                  95

```
Ala Phe Met Glu His Val Glu Glu Leu Ile Asp Thr Lys Ile Gly
            100                 105                 110

Tyr Ala Lys Asn Lys Ala Leu Ser Glu Leu Ala Gly Ile Gln Arg Asn
        115                 120                 125

Leu Glu Thr Tyr Ile Gln Leu Arg Asn Glu Trp Glu Asn Asp Ile Glu
    130                 135                 140

Asn Ser Lys Ala Gln Gly Lys Val Ala Asn Tyr Tyr Glu Ser Leu Glu
145                 150                 155                 160

Gln Ala Val Glu Arg Ser Met Pro Gln Phe Ala Val Glu Asn Phe Glu
                165                 170                 175

Val Pro Leu Leu Thr Val Tyr Val Gln Ala Ala Asn Leu His Leu Leu
            180                 185                 190

Leu Leu Arg Asp Val Ser Val Tyr Gly Lys Cys Trp Gly Trp Ser Glu
        195                 200                 205

Gln Lys Ile Lys Ile Tyr Tyr Asp Lys Gln Ile Lys Tyr Thr His Glu
    210                 215                 220

Tyr Thr Asn His Cys Val Asn Trp Tyr Asn Lys Gly Leu Glu Arg Leu
225                 230                 235                 240

Lys Asn Lys Gly Ser Ser Tyr Gln Asp Trp Tyr Asn Tyr Asn Arg Phe
                245                 250                 255

Arg Arg Glu Met Thr Leu Thr Val Leu Asp Ile Val Ala Leu Phe Pro
            260                 265                 270

His Tyr Asp Val Gln Thr Tyr Pro Ile Thr Thr Val Ala Gln Leu Thr
        275                 280                 285

Arg Glu Val Tyr Thr Asp Pro Leu Leu Asn Phe Asn Pro Lys Leu His
    290                 295                 300

Ser Val Ser Gln Leu Pro Ser Phe Ser Asp Met Glu Asn Ala Thr Ile
305                 310                 315                 320

Arg Thr Pro His Leu Met Glu Phe Leu Arg Met Leu Thr Ile Tyr Thr
                325                 330                 335

Asp Trp Tyr Ser Val Gly Arg Asn Tyr Tyr Trp Gly His Arg Val
            340                 345                 350

Thr Ser Tyr His Val Gly Gly Glu Asn Ile Arg Ser Pro Leu Tyr Gly
        355                 360                 365

Arg Glu Ala Asn Gln Glu Val Pro Arg Asp Phe Tyr Phe Tyr Gly Pro
    370                 375                 380

Val Phe Lys Thr Leu Ser Lys Pro Thr Leu Arg Pro Leu Gln Gln Pro
385                 390                 395                 400

Ala Pro Ala Pro Pro Phe Asn Leu Arg Ser Leu Glu Gly Val Glu Phe
                405                 410                 415

His Thr Pro Thr Gly Ser Phe Met Tyr Arg Glu Arg Gly Ser Val Asp
            420                 425                 430

Ser Phe Asn Glu Leu Pro Pro Phe Asn Pro Val Gly Leu Pro His Lys
        435                 440                 445

Val Tyr Ser His Arg Leu Cys His Ala Thr Phe Val Arg Lys Ser Gly
    450                 455                 460

Thr Pro Tyr Leu Thr Thr Gly Ala Ile Phe Ser Trp Thr His Arg Ser
465                 470                 475                 480

Ala Glu Glu Thr Asn Thr Ile Glu Ser Asn Ile Ile Thr Gln Ile Pro
                485                 490                 495

Leu Val Lys Ala Tyr Gln Ile Gly Ser Gly Thr Thr Val Arg Lys Gly
            500                 505                 510

Pro Gly Phe Thr Gly Gly Asp Ile Leu Arg Arg Thr Gly Pro Gly Thr
        515                 520                 525
```

```
Phe Gly Asp Met Arg Ile Asn Ile Asn Ala Pro Leu Ser Gln Arg Tyr
        530                 535                 540

Arg Val Arg Ile Arg Tyr Ala Ser Thr Thr Asp Leu Gln Phe Val Thr
545                 550                 555                 560

Ser Ile Asn Gly Thr Thr Ile Asn Ile Gly Asn Phe Pro Lys Thr Ile
                565                 570                 575

Asn Asn Leu Asn Thr Leu Gly Ser Glu Gly Tyr Arg Thr Val Ser Phe
            580                 585                 590

Ser Thr Pro Phe Ser Phe Ser Asn Ala Gln Ser Ile Phe Arg Leu Gly
        595                 600                 605

Ile Gln Ala Phe Ser Gly Val Gln Glu Val Tyr Val Asp Lys Ile Glu
    610                 615                 620

Phe Ile Pro Val Glu
625

<210> SEQ ID NO 4
<211> LENGTH: 1806
<212> TYPE: DNA
<213> ORGANISM: Artificial Sequence
<220> FEATURE:
<223> OTHER INFORMATION: synthetic nucleotide sequence encoding
      AXMI-004B-2M (synaxmi-004B-2m)

<400> SEQUENCE: 4
```

| | | | | | |
|---|---|---|---|---|---|
| atgaactcaa | aggagcatga | ttacctcaag | gtctgcaacg | atctctccga | tgccaacatc | 60 |
| aacatggagc | gcttcgataa | gaacgatgcc | ctcgagatcg | gcatgtccat | cgtctccgag | 120 |
| ctcatcggca | tgatccccgg | cggcaccgcc | ctgcagttcg | tcttcaacca | gctctggagc | 180 |
| cgcctcggcg | actcaggctg | gaacgctttc | atggagcatg | tcgaggagct | catcgatacc | 240 |
| aagatcgagg | gctacgccaa | gaacaaggcc | ctgtccgagc | tggccggtat | ccagcgtaac | 300 |
| ctggagacct | acatccagct | gaggaacgag | tgggagaacg | atatcgagaa | ctccaaggcc | 360 |
| cagggcaagg | tcgctaacta | ctacgagagc | ctggagcagg | ccgtcgagcg | ttcaatgcct | 420 |
| cagttcgccg | ttgagaactt | cgaggtcccc | ttgctgaccg | tctacgtcca | ggctgctaac | 480 |
| ctccatctcc | tgctcctcag | ggatgtcagc | gtttacggca | agtgctgggg | ttggtctgag | 540 |
| cagaagatca | gatctactac | cgataagcag | atcaagtaca | cccatgagta | caccaaccat | 600 |
| tgcgtcaact | ggtacaacaa | gggcctggag | cgcctgaaga | caagggctc | aagctaccag | 660 |
| gattggtaca | actacaaccg | cttccgccgc | gagatgaccc | tgaccgtcct | cgatatcgtc | 720 |
| gccctgttcc | cccattacga | tgtccagacc | taccccatca | ccaccgtcgc | ccagctcacc | 780 |
| cgcgaggtct | acactgatcc | cctcctgaac | ttcaacccca | agctccattc | agtcagccag | 840 |
| ctgcccagct | tcagcgatat | ggagaacgcc | accatccgca | ccccccatct | gatggagttc | 900 |
| ctgcgcatgc | tgaccatcta | caccgattgg | tacagcgtcg | gccgcaacta | ctactggggc | 960 |
| ggccatcgcg | tcacctcata | ccatgtcggc | ggcgagaaca | tccgctctcc | tctgtacggt | 1020 |
| agggaggcta | accaggaggt | ccctagggat | ttctacttct | acggcccccgt | cttcaagacc | 1080 |
| ctgtccaagc | ccaccctgag | gcctttgcag | cagcctgctc | ctgctcctcc | tttcaacttg | 1140 |
| cgttctctgg | agggtgttga | gttccatacc | cccaccggtt | cattcatgta | ccgcgagcgc | 1200 |
| ggttctgtcg | atagcttcaa | cgagctgccc | ctttcaacc | ccgtcggttt | gcctcataag | 1260 |
| gtctacagcc | atcgcctgtg | ccatgccacc | ttcgtccgta | agagcggcac | cccttacctg | 1320 |
| accaccggtg | ctatcttctc | ctggaccccat | aggtccgctg | aggagactaa | caccatcgag | 1380 |
| tcaaacatca | tcacccagat | cccccctcgtc | aaggcctacc | agatcggcag | cggcaccacc | 1440 |

-continued

```
gtccgtaagg gtcctggttt caccggtggt gatatcctca ggcgtaccgg tcctggtact   1500
ttcggtgata tgaggatcaa catcaacgcc cccctctccc agaggtacag ggtccgtatc   1560
cgttacgcct ctaccaccga tctgcagttc gtcacctcaa tcaacggcac caccatcaac   1620
atcggcaact cccccaagac catcaacaac ctgaacaccc tgggctccga gggctaccgc   1680
accgtctctt tctccacccc tttcagcttc tctaacgccc agtccatctt ccgcctcggt   1740
atccaggctt tcagcggtgt ccaggaggtt tacgtcgata agatcgagtt catccccgtc   1800
gagtga                                                              1806
```

<210> SEQ ID NO 5
<211> LENGTH: 601
<212> TYPE: PRT
<213> ORGANISM: Bacillus thuringiensis

<400> SEQUENCE: 5

```
Met Asn Ser Lys Glu His Asp Tyr Leu Lys Val Cys Asn Asp Leu Ser
 1               5                  10                  15

Asp Ala Asn Ile Asn Met Glu Arg Phe Asp Lys Asn Asp Ala Leu Glu
            20                  25                  30

Ile Gly Met Ser Ile Val Ser Glu Leu Ile Gly Met Ile Pro Gly Gly
        35                  40                  45

Thr Ala Leu Gln Phe Val Phe Asn Gln Leu Trp Ser Arg Leu Gly Asp
    50                  55                  60

Ser Gly Trp Asn Ala Phe Met Glu His Val Glu Glu Leu Ile Asp Thr
65                  70                  75                  80

Lys Ile Glu Gly Tyr Ala Lys Asn Lys Ala Leu Ser Glu Leu Ala Gly
                85                  90                  95

Ile Gln Arg Asn Leu Glu Thr Tyr Ile Gln Leu Arg Asn Glu Trp Glu
            100                 105                 110

Asn Asp Ile Glu Asn Ser Lys Ala Gln Gly Lys Val Ala Asn Tyr Tyr
        115                 120                 125

Glu Ser Leu Glu Gln Ala Val Glu Arg Ser Met Pro Gln Phe Ala Val
    130                 135                 140

Glu Asn Phe Glu Val Pro Leu Leu Thr Val Tyr Val Gln Ala Ala Asn
145                 150                 155                 160

Leu His Leu Leu Leu Leu Arg Asp Val Ser Val Tyr Gly Lys Cys Trp
                165                 170                 175

Gly Trp Ser Glu Gln Lys Ile Lys Ile Tyr Tyr Asp Lys Gln Ile Lys
            180                 185                 190

Tyr Thr His Glu Tyr Thr Asn His Cys Val Asn Trp Tyr Asn Lys Gly
        195                 200                 205

Leu Glu Arg Leu Lys Asn Lys Gly Ser Ser Tyr Gln Asp Trp Tyr Asn
    210                 215                 220

Tyr Asn Arg Phe Arg Arg Glu Met Thr Leu Thr Val Leu Asp Ile Val
225                 230                 235                 240

Ala Leu Phe Pro His Tyr Asp Val Gln Thr Tyr Pro Ile Thr Thr Val
                245                 250                 255

Ala Gln Leu Thr Arg Glu Val Tyr Thr Asp Pro Leu Leu Asn Phe Asn
            260                 265                 270

Pro Lys Leu His Ser Val Ser Gln Leu Pro Ser Phe Ser Asp Met Glu
        275                 280                 285

Asn Ala Thr Ile Arg Thr Pro His Leu Met Glu Phe Leu Arg Met Leu
    290                 295                 300
```

Thr Ile Tyr Thr Asp Trp Tyr Ser Val Gly Arg Asn Tyr Tyr Trp Gly
305                 310                 315                 320

Gly His Arg Val Thr Ser Tyr His Val Gly Glu Asn Ile Arg Ser
            325                 330                 335

Pro Leu Tyr Gly Arg Glu Ala Asn Gln Glu Val Pro Arg Asp Phe Tyr
            340                 345                 350

Phe Tyr Gly Pro Val Phe Lys Thr Leu Ser Lys Pro Thr Leu Arg Pro
            355                 360                 365

Leu Gln Gln Pro Ala Pro Ala Pro Pro Phe Asn Leu Arg Ser Leu Glu
370                 375                 380

Gly Val Glu Phe His Thr Pro Thr Gly Ser Phe Met Tyr Arg Glu Arg
385                 390                 395                 400

Gly Ser Val Asp Ser Phe Asn Glu Leu Pro Pro Phe Asn Pro Val Gly
            405                 410                 415

Leu Pro His Lys Val Tyr Ser His Arg Leu Cys His Ala Thr Phe Val
            420                 425                 430

Arg Lys Ser Gly Thr Pro Tyr Leu Thr Thr Gly Ala Ile Phe Ser Trp
            435                 440                 445

Thr His Arg Ser Ala Glu Glu Thr Asn Thr Ile Glu Ser Asn Ile Ile
450                 455                 460

Thr Gln Ile Pro Leu Val Lys Ala Tyr Gln Ile Gly Ser Gly Thr Thr
465                 470                 475                 480

Val Arg Lys Gly Pro Gly Phe Thr Gly Gly Asp Ile Leu Arg Arg Thr
            485                 490                 495

Gly Pro Gly Thr Phe Gly Asp Met Arg Ile Asn Ile Asn Ala Pro Leu
            500                 505                 510

Ser Gln Arg Tyr Arg Val Arg Ile Arg Tyr Ala Ser Thr Thr Asp Leu
            515                 520                 525

Gln Phe Val Thr Ser Ile Asn Gly Thr Thr Ile Asn Ile Gly Asn Phe
530                 535                 540

Pro Lys Thr Ile Asn Asn Leu Asn Thr Leu Gly Ser Glu Gly Tyr Arg
545                 550                 555                 560

Thr Val Ser Phe Ser Thr Pro Phe Ser Phe Ser Asn Ala Gln Ser Ile
            565                 570                 575

Phe Arg Leu Gly Ile Gln Ala Phe Ser Gly Val Gln Glu Val Tyr Val
            580                 585                 590

Asp Lys Ile Glu Phe Ile Pro Val Glu
            595                 600

<210> SEQ ID NO 6
<211> LENGTH: 1743
<212> TYPE: DNA
<213> ORGANISM: Artificial Sequence
<220> FEATURE:
<223> OTHER INFORMATION: synthetic nucleotide sequence encoding
      AXMI-004B-3M (synaxmi-004B-3m)

<400> SEQUENCE: 6
atggagcgct tcgataagaa cgatgcccte gagatcggca tgtccatcgt ctccgagctc      60
atcggcatga tccccggcgg caccgccctg cagttcgtct tcaaccagct ctggagccgc     120
ctcggcgact caggctggaa cgctttcatg gagcatgtcg aggagctcat cgataccaag     180
atcgagggct acgccaagaa caaggccctg tccgagctgg ccggtatcca gcgtaacctg     240
gagacctaca tccagctgag gaacgagtgg gagaacgata tcgagaactc caaggcccag     300
ggcaaggtcg ctaactacta cgagagcctg gagcaggccg tcgagcgttc aatgcctcag     360

```
ttcgccgttg agaacttcga ggtccccttg ctgaccgtct acgtccaggc tgctaacctc    420
catctcctgc tcctcaggga tgtcagcgtt tacggcaagt gctggggttg gtctgagcag    480
aagatcaaga tctactacga taagcagatc aagtacaccc atgagtacac caaccattgc    540
gtcaactggt acaacaaggg cctggagcgc ctgaagaaca agggctcaag ctaccaggat    600
tggtacaact acaaccgctt ccgccgcgag atgaccctga ccgtcctcga tatcgtcgcc    660
ctgttccccc attacgatgt ccagacctac cccatcacca ccgtcgccca gctcacccgc    720
gaggtctaca ctgatcccct cctgaacttc aaccccaagc tccattcagt cagccagctg    780
cccagcttca gcgatatgga gaacgccacc atccgcaccc ccatctgat ggagttcctg     840
cgcatgctga ccatctacac cgattggtac agcgtcggcc gcaactacta ctggggcggc    900
catcgcgtca cctcatacca tgtcggcggc gagaacatcc gctctcctct gtacggtagg    960
gaggctaacc aggaggtccc tagggatttc tacttctacg ccccgtcttc aagaccctg    1020
tccaagccca ccctgaggcc tttgcagcag cctgctcctg ctcctccttt caacttgcgt   1080
tctctggagg gtgttgagtt ccatacccccc accggttcat tcatgtaccg cgagcgcggt   1140
tctgtcgata gcttcaacga gctgcccct ttcaacccccg tcggtttgcc tcataaggtc    1200
tacagccatc gcctgtgcca tgccaccttc gtccgtaaga gcggcacccc ttacctgacc   1260
accggtgcta tcttctcctg gacccatagg tccgctgagg agactaacac catcgagtca   1320
aacatcatca cccagatccc cctcgtcaag gcctaccaga tcggcagcgg caccaccgtc   1380
cgtaagggtc ctggtttcac cggtggtgat atcctcaggc gtaccggtcc tggtactttc   1440
ggtgatatga ggatcaacat caacgccccc ctctcccaga ggtacagggt ccgtatccgt   1500
tacgcctcta ccaccgatct gcagttcgtc acctcaatca acggcaccac catcaacatc   1560
ggcaacttcc ccaagaccat caacaacctg aacaccctgg gctccgaggg ctaccgcacc   1620
gtctctttct ccacccctt cagcttctct aacgcccagt ccatcttccg cctcggtatc    1680
caggctttca gcggtgtcca ggaggtttac gtcgataaga tcgagttcat ccccgtcgag   1740
tga                                                                  1743
```

<210> SEQ ID NO 7
<211> LENGTH: 1743
<212> TYPE: DNA
<213> ORGANISM: Artificial Sequence
<220> FEATURE:
<223> OTHER INFORMATION: synthetic nucleotide sequence encoding
    AXMI-004B-3M (synaxmi-004C-3m)

<400> SEQUENCE: 7

```
atggagagat tgacaagaa tgatgctctg gagattggga tgagcatcgt ctccgagctg      60
attgggatga ttcctggagg gacggcgctg caatttgtct tcaatcagct gtggtcaagg    120
ctggagagatt ctggatggaa tgccttcatg gagcatgtgg aggagctcat cgacaccaag   180
attgaaggat atgccaagaa caaggcgctc tcagagctgg ccggcatcca gaggaacctg    240
gagacctaca tccagctgag gaatgaatgg gagaatgaca tcgagaacag caaggctcaa    300
ggcaaggtgg ccaactacta cgagagcttg agcaagctg ttgaaagatc aatgcctcaa     360
tttgctgtgg agaacttcga ggtgccgctg ctcaccgtct atgttcaagc tgccaacctc    420
cacctgctgc tgctgagaga tgtttcagtt tatggaaaat gctggggctg gagcgagcag    480
aagatcaaga tctactacga caagcagatc aagtacaccc atgagtacac caaccactgc    540
gtcaactggt acaacaaggg gctggagagg ctgaagaaca agggctcaag ctaccaagat    600
tggtacaact acaacaggtt cagaagggag atgacattga cggtgctgga catcgtggcg    660
```

-continued

```
ctcttccctc attatgatgt tcaaacctac cccatcacca ccgtggcgca gctgacaaga    720
gaagtctaca ccgacccgct gctaaacttc aaccccaagc tgcattctgt gagccagctg    780
ccgagcttct ccgacatgga gaatgccacc atcaggacgc cgcacctgat ggagttcttg    840
aggatgctca ccatctacac tgattggtat tctgttggaa ggaactacta ctggggcggc    900
caccgcgtca cctcatatca tgttggtggt gagaacatcc gctcgccgct ctatggaaga    960
gaagcaaatc aagaagttcc aagagatttc tacttctatg gacctgtctt caagaccttg   1020
tcaaagccaa cattgaggcc gctccagcag ccggcgccgg cgccgccctt caacctgagg   1080
agcttggaag gagttgagtt ccacacgcca actggcagct tcatgtacag agaaagagga   1140
tcagtggaca gcttcaacga gctgccgccc ttcaaccctg ttgggctgcc gcacaaggtc   1200
tacagccacc gcctctgcca tgccaccttc gtgaggaaga gcggcacgcc gtacctcacc   1260
accggcgcca tcttctcatg gacccaccgc tctgctgaag aaaccaacac catcgagagc   1320
aacatcatca cccagatccc gctggtgaag gcctaccaga ttggatcagg caccaccgtg   1380
aggaaaggac ctggcttcac tggaggagac atcttgagga ggactggacc tggaacattt   1440
ggagacatga ggatcaacat caacgcgccg ctgagccaaa gatacagggt gaggatcaga   1500
tatgcttcaa caactgatct tcaatttgtg acaagcatca atggcaccac catcaacatc   1560
ggcaacttcc ccaagaccat caacaacctc aacaccttgg gctcagaagg ctacaggacg   1620
gtgagcttct ccacgcccct tcagcttcag caatgctcaa agcatcttcc cctcggcatc   1680
caagccttct ctggagttca agaagtttat gtggacaaga ttgagttcat cccggtggag   1740
taa                                                                 1743
```

```
<210> SEQ ID NO 8
<211> LENGTH: 1743
<212> TYPE: DNA
<213> ORGANISM: Artificial Sequence
<220> FEATURE:
<223> OTHER INFORMATION: synthetic nucleotide sequence encoding
      AXMI-004B-3M (synaxmi-004D-3m)

<400> SEQUENCE: 8
```

```
atggaaagat tgacaagaa tgatgctctg gagattggga tgagcatcgt ctccgagctg     60
attgggatga ttcctggagg aacggcgctg caatttgtct tcaatcagct gtggtcaagg    120
cttggagatt ctggatggaa tgccttcatg gagcatgtgg aggagctcat cgacaccaag    180
attgaaggat atgccaagaa caaggcgctc tcagagctgg ctggcatcca agaaatttg     240 gagacctaca tccagctgag aaatgaatgg gaaaatgaca ttgagaacag caaggctcaa    300
ggaaaggtgg ccaactacta tgagagcttg agcaagctg ttgaaagatc aatgcctcaa     360
tttgctgtgg agaacttcga ggtgccgctg ctcaccgtct atgttcaagc tgccaacctc    420
cacctgctgc tgctgagaga tgtttcagtt tatggaaaat gctggggatg gagcgagcag    480
aagatcaaga tctactacga caagcagatc aagtacactc atgagtacac caaccattgt    540
gtcaactggt acaacaaagg actgagagg ctgaagaaca aggatcaag ctaccaagat      600 tggtacaact acaacagatt cagaagagag atgacattga cagtgctgga cattgtggcg    660
ctcttccctc attatgatgt tcaaacctac cccatcacca ccgtggcgca gctgacaaga    720
gaagtctaca ccgacccgct gctaaacttc aaccccaagc tgcattctgt gagccagctg    780
ccatccttct ccgacatgga aaatgccacc atcaggacgc cgcacctgat ggagttcttg    840
aggatgctca ccatctacac tgattggtat tctgttggaa gaaactacta ctggggcggc    900
```

-continued

```
caccgcgtga catcatatca tgttggtggt gaaaacatca gatcgccgct ctatggaaga    960
gaagcaaatc aagaagttcc aagagatttc tacttctatg acctgtctt caagacattg   1020
tcaaagccaa cattgaggcc gctccagcag ccggcgccgg cgccgccatt caacttgagg   1080
agcttggaag gagttgagtt ccacacacca actggcagct tcatgtacag agaaagagga   1140
tcagtggaca gcttcaatga gctgccgcca ttcaaccctg ttgggcttcc tcacaaggtc   1200
tacagccacc gcctctgcca tgcaaccttc gtgaggaaga gcggcacgcc gtacctcacc   1260
accggcgcca tcttctcatg acccaccgc tctgctgaag aaacaaacac catcgagagc   1320
aacatcatca cccagatccc gctggtgaag gcctaccaaa ttggatcagg aacaacagtg   1380
aggaaaggac ctggcttcac tggaggagac atcttgagaa gaactggacc tggaacattt   1440
ggagacatga ggatcaacat caacgcgccg ctgagccaaa gatacagggt gaggatcaga   1500
tatgcttcaa caactgatct tcaatttgtg acaagcatca atggcaccac catcaacatc   1560
ggcaacttcc ccaagaccat caacaacctc aacaccttgg gctcagaagg ctacaggacg   1620
gtgagcttct ccacgccatt cagcttctca aatgctcaaa gcatcttccg cctcggcatc   1680
caagccttct ctggagttca agaagtttat gtggacaaga ttgagttcat cccggtggaa   1740
taa                                                                1743
```

<210> SEQ ID NO 9
<211> LENGTH: 580
<212> TYPE: PRT
<213> ORGANISM: Bacillus thuringiensis

<400> SEQUENCE: 9

```
Met Glu Arg Phe Asp Lys Asn Asp Ala Leu Glu Ile Gly Met Ser Ile
  1               5                  10                  15

Val Ser Glu Leu Ile Gly Met Ile Pro Gly Gly Thr Ala Leu Gln Phe
             20                  25                  30

Val Phe Asn Gln Leu Trp Ser Arg Leu Gly Asp Ser Gly Trp Asn Ala
         35                  40                  45

Phe Met Glu His Val Glu Glu Leu Ile Asp Thr Lys Ile Glu Gly Tyr
     50                  55                  60

Ala Lys Asn Lys Ala Leu Ser Glu Leu Ala Gly Ile Gln Arg Asn Leu
 65                  70                  75                  80

Glu Thr Tyr Ile Gln Leu Arg Asn Glu Trp Glu Asn Asp Ile Glu Asn
                 85                  90                  95

Ser Lys Ala Gln Gly Lys Val Ala Asn Tyr Tyr Glu Ser Leu Glu Gln
            100                 105                 110

Ala Val Glu Arg Ser Met Pro Gln Phe Ala Val Glu Asn Phe Glu Val
        115                 120                 125

Pro Leu Leu Thr Val Tyr Val Gln Ala Ala Asn Leu His Leu Leu Leu
    130                 135                 140

Leu Arg Asp Val Ser Val Tyr Gly Lys Cys Trp Gly Trp Ser Glu Gln
145                 150                 155                 160

Lys Ile Lys Ile Tyr Tyr Asp Lys Gln Ile Lys Tyr Thr His Glu Tyr
                165                 170                 175

Thr Asn His Cys Val Asn Trp Tyr Asn Lys Gly Leu Glu Arg Leu Lys
            180                 185                 190

Asn Lys Gly Ser Ser Tyr Gln Asp Trp Tyr Asn Tyr Asn Arg Phe Arg
        195                 200                 205

Arg Glu Met Thr Leu Thr Val Leu Asp Ile Val Ala Leu Phe Pro His
    210                 215                 220
```

-continued

```
Tyr Asp Val Gln Thr Tyr Pro Ile Thr Thr Val Ala Gln Leu Thr Arg
225                 230                 235                 240

Glu Val Tyr Thr Asp Pro Leu Leu Asn Phe Asn Pro Lys Leu His Ser
            245                 250                 255

Val Ser Gln Leu Pro Ser Phe Ser Asp Met Glu Asn Ala Thr Ile Arg
        260                 265                 270

Thr Pro His Leu Met Glu Phe Leu Arg Met Leu Thr Ile Tyr Thr Asp
    275                 280                 285

Trp Tyr Ser Val Gly Arg Asn Tyr Tyr Trp Gly Gly His Arg Val Thr
290                 295                 300

Ser Tyr His Val Gly Gly Glu Asn Ile Arg Ser Pro Leu Tyr Gly Arg
305                 310                 315                 320

Glu Ala Asn Gln Glu Val Pro Arg Asp Phe Tyr Phe Tyr Gly Pro Val
            325                 330                 335

Phe Lys Thr Leu Ser Lys Pro Thr Leu Arg Pro Leu Gln Gln Pro Ala
        340                 345                 350

Pro Ala Pro Pro Phe Asn Leu Arg Ser Leu Glu Gly Val Glu Phe His
    355                 360                 365

Thr Pro Thr Gly Ser Phe Met Tyr Arg Glu Arg Gly Ser Val Asp Ser
370                 375                 380

Phe Asn Glu Leu Pro Pro Phe Asn Pro Val Gly Leu Pro His Lys Val
385                 390                 395                 400

Tyr Ser His Arg Leu Cys His Ala Thr Phe Val Arg Lys Ser Gly Thr
            405                 410                 415

Pro Tyr Leu Thr Thr Gly Ala Ile Phe Ser Trp Thr His Arg Ser Ala
        420                 425                 430

Glu Glu Thr Asn Thr Ile Glu Ser Asn Ile Ile Thr Gln Ile Pro Leu
    435                 440                 445

Val Lys Ala Tyr Gln Ile Gly Ser Gly Thr Thr Val Arg Lys Gly Pro
450                 455                 460

Gly Phe Thr Gly Gly Asp Ile Leu Arg Arg Thr Gly Pro Gly Thr Phe
465                 470                 475                 480

Gly Asp Met Arg Ile Asn Ile Asn Ala Pro Leu Ser Gln Arg Tyr Arg
            485                 490                 495

Val Arg Ile Arg Tyr Ala Ser Thr Thr Asp Leu Gln Phe Val Thr Ser
        500                 505                 510

Ile Asn Gly Thr Thr Ile Asn Ile Gly Asn Phe Pro Lys Thr Ile Asn
    515                 520                 525

Asn Leu Asn Thr Leu Gly Ser Glu Gly Tyr Arg Thr Val Ser Phe Ser
530                 535                 540

Thr Pro Phe Ser Phe Ser Asn Ala Gln Ser Ile Phe Arg Leu Gly Ile
545                 550                 555                 560

Gln Ala Phe Ser Gly Val Gln Glu Val Tyr Val Asp Lys Ile Glu Phe
            565                 570                 575

Ile Pro Val Glu
            580
```

<210> SEQ ID NO 10
<211> LENGTH: 1809
<212> TYPE: DNA
<213> ORGANISM: Artificial Sequence
<220> FEATURE:
<223> OTHER INFORMATION: synthetic nucleotide sequence encoding
      AXMI-004B-3M-ALT1 (synaxmi-004B-3m-alt1)

<400> SEQUENCE: 10

```
atgaaggtga caatccagcc tggcgatctc acaggcatca ttcagagccc agcgtcaaag    60
tcttcaatgg agcgcttcga taagaacgat gccctcgaga tcggcatgtc catcgtctcc   120
gagctcatcg gcatgatccc cggcggcacc gccctgcagt tcgtcttcaa ccagctctgg   180
agccgcctcg gcgactcagg ctggaacgct ttcatggagc atgtcgagga gctcatcgat   240
accaagatcg agggctacgc caagaacaag gccctgtccg agctggccgg tatccagcgt   300
aacctggaga cctacatcca gctgaggaac gagtgggaga cgatatcga gaactccaag   360 gcccagggca aggtcgctaa ctactacgag agcctggagc aggccgtcga gcgttcaatg   420
cctcagttcg ccgttgagaa cttcgaggtc cccttgctga ccgtctacgt ccaggctgct   480
aacctccatc tcctgctcct cagggatgtc agcgtttacg caagtgctg gggttggtct    540 gagcagaaga tcaagatcta ctacgataag cagatcaagt acacccatga gtacaccaac   600
cattgcgtca actggtacaa caagggcctg agcgcctga gaacaagggg ctcaagctac    660
caggattggt acaactacaa ccgcttccgc cgcgagatga ccctgaccgt cctcgatatc   720
gtcgccctgt cccccattac gatgtccag acctacccca tcaccaccgt cgcccagctc   780
acccgcgagg tctacactga tccccctcctg aacttcaacc ccaagctcca ttcagtcagc   840
cagctgccca gcttcagcga tatggagaac gccaccatcc gcacccccca tctgatggag   900
ttcctgcgca tgctgaccat ctacaccgat tggtacagcg tcggccgcaa ctactactgg   960
ggcggccatc gcgtcacctc ataccatgtc ggcggcgaga acatccgctc tcctctgtac  1020 ggtaggagg ctaaccagga ggtccctagg gatttctact tctacggccc cgtcttcaag   1080
accctgtcca agcccaccct gaggccttg cagcagcctg ctcctgctcc tccttttcaac  1140 ttgcgttctc tggagggtgt tgagttccat accccaccg gttcattcat gtaccgcgag   1200
cgcggttctg tcgatagctt caacgagctg ccccctttca ccccgtcgg tttgcctcat   1260 aaggtctaca gccatcgcct gtgccatgcc accttcgtcc gtaagagcgg caccccttac   1320
ctgaccaccg gtgctatctt ctcctggacc cataggtccg ctgaggagac taacaccatc  1380
gagtcaaaca tcatcaccca gatccccctc gtcaaggcct accagatcgg cagcggcacc   1440
accgtccgta agggtcctgg tttcaccggt ggtgatatcc tcaggcgtac cggtcctggt   1500
actttcggtg atatgaggat caacatcaac gccccctct cccagaggta cagggtccgt    1560
atccgttacg cctctaccac cgatctgcag ttcgtcacct caatcaacgg caccaccatc   1620
aacatcggca acttccccaa gaccatcaac aacctgaaca ccctgggctc cgagggctac   1680
cgcaccgtct ctttctccac ccctttcagc ttctctaacg cccagtccat cttccgcctc   1740
ggtatccagg ctttcagcgg tgtccaggag gtttacgtcg ataagatcga gttcatcccc   1800
gtcgagtga                                                          1809
```

<210> SEQ ID NO 11
<211> LENGTH: 602
<212> TYPE: PRT
<213> ORGANISM: Artificial Sequence
<220> FEATURE:
<223> OTHER INFORMATION: variant AXMI-004B-3M sequence (AXMI-004B-3M-ALT1)

<400> SEQUENCE: 11

Met Lys Val Thr Ile Gln Pro Gly Asp Leu Thr Gly Ile Ile Gln Ser
1               5                   10                  15

Pro Ala Ser Lys Ser Ser Met Glu Arg Phe Asp Lys Asn Asp Ala Leu
            20                  25                  30

Glu Ile Gly Met Ser Ile Val Ser Glu Leu Ile Gly Met Ile Pro Gly

-continued

```
                35                   40                  45
Gly Thr Ala Leu Gln Phe Val Phe Asn Gln Leu Trp Ser Arg Leu Gly
         50                   55                  60

Asp Ser Gly Trp Asn Ala Phe Met Glu His Val Glu Leu Ile Asp
 65                  70                  75                  80

Thr Lys Ile Glu Gly Tyr Ala Lys Asn Lys Ala Leu Ser Glu Leu Ala
                 85                  90                  95

Gly Ile Gln Arg Asn Leu Glu Thr Tyr Ile Gln Leu Arg Asn Glu Trp
                100                 105                 110

Glu Asn Asp Ile Glu Asn Ser Lys Ala Gln Gly Lys Val Ala Asn Tyr
                115                 120                 125

Tyr Glu Ser Leu Glu Gln Ala Val Glu Arg Ser Met Pro Gln Phe Ala
                130                 135                 140

Val Glu Asn Phe Glu Val Pro Leu Leu Thr Val Tyr Val Gln Ala Ala
145                 150                 155                 160

Asn Leu His Leu Leu Leu Arg Asp Val Ser Val Tyr Gly Lys Cys
                165                 170                 175

Trp Gly Trp Ser Glu Gln Lys Ile Lys Ile Tyr Tyr Asp Lys Gln Ile
                180                 185                 190

Lys Tyr Thr His Glu Tyr Thr Asn His Cys Val Asn Trp Tyr Asn Lys
                195                 200                 205

Gly Leu Glu Arg Leu Lys Asn Lys Gly Ser Ser Tyr Gln Asp Trp Tyr
                210                 215                 220

Asn Tyr Asn Arg Phe Arg Arg Glu Met Thr Leu Thr Val Leu Asp Ile
225                 230                 235                 240

Val Ala Leu Phe Pro His Tyr Asp Val Gln Thr Tyr Pro Ile Thr Thr
                245                 250                 255

Val Ala Gln Leu Thr Arg Glu Val Tyr Thr Asp Pro Leu Leu Asn Phe
                260                 265                 270

Asn Pro Lys Leu His Ser Val Ser Gln Leu Pro Ser Phe Ser Asp Met
                275                 280                 285

Glu Asn Ala Thr Ile Arg Thr Pro His Leu Met Glu Phe Leu Arg Met
290                 295                 300

Leu Thr Ile Tyr Thr Asp Trp Tyr Ser Val Gly Arg Asn Tyr Tyr Trp
305                 310                 315                 320

Gly Gly His Arg Val Thr Ser Tyr His Val Gly Gly Glu Asn Ile Arg
                325                 330                 335

Ser Pro Leu Tyr Gly Arg Glu Ala Asn Gln Glu Val Pro Arg Asp Phe
                340                 345                 350

Tyr Phe Tyr Gly Pro Val Phe Lys Thr Leu Ser Lys Pro Thr Leu Arg
                355                 360                 365

Pro Leu Gln Gln Pro Ala Pro Ala Pro Pro Phe Asn Leu Arg Ser Leu
                370                 375                 380

Glu Gly Val Glu Phe His Thr Pro Thr Gly Ser Phe Met Tyr Arg Glu
385                 390                 395                 400

Arg Gly Ser Val Asp Ser Phe Asn Glu Leu Pro Pro Phe Asn Pro Val
                405                 410                 415

Gly Leu Pro His Lys Val Tyr Ser His Arg Leu Cys His Ala Thr Phe
                420                 425                 430

Val Arg Lys Ser Gly Thr Pro Tyr Leu Thr Thr Gly Ala Ile Phe Ser
                435                 440                 445

Trp Thr His Arg Ser Ala Glu Glu Thr Asn Thr Ile Glu Ser Asn Ile
                450                 455                 460
```

```
Ile Thr Gln Ile Pro Leu Val Lys Ala Tyr Gln Ile Gly Ser Gly Thr
465                 470                 475                 480

Thr Val Arg Lys Gly Pro Gly Phe Thr Gly Gly Asp Ile Leu Arg Arg
                485                 490                 495

Thr Gly Pro Gly Thr Phe Gly Asp Met Arg Ile Asn Ile Asn Ala Pro
            500                 505                 510

Leu Ser Gln Arg Tyr Arg Val Arg Ile Arg Tyr Ala Ser Thr Thr Asp
        515                 520                 525

Leu Gln Phe Val Thr Ser Ile Asn Gly Thr Thr Ile Asn Ile Gly Asn
    530                 535                 540

Phe Pro Lys Thr Ile Asn Asn Leu Asn Thr Leu Gly Ser Glu Gly Tyr
545                 550                 555                 560

Arg Thr Val Ser Phe Ser Thr Pro Phe Ser Phe Ser Asn Ala Gln Ser
                565                 570                 575

Ile Phe Arg Leu Gly Ile Gln Ala Phe Ser Gly Val Gln Glu Val Tyr
            580                 585                 590

Val Asp Lys Ile Glu Phe Ile Pro Val Glu
        595                 600
```

<210> SEQ ID NO 12
<211> LENGTH: 1752
<212> TYPE: DNA
<213> ORGANISM: Artificial Sequence
<220> FEATURE:
<223> OTHER INFORMATION: synthetic nucleotide sequence encoding
    AXMI-004B-3M-ALT2 (synaxmi-004B-3m-alt2)

<400> SEQUENCE: 12

```
atggcggcga tggagcgctt cgataagaac gatgccctcg agatcggcat gtccatcgtc      60
tccgagctca tcggcatgat ccccggcggc accgccctgc agttcgtctt caaccagctc     120
tggagccgcc tcggcgactc aggctggaac gctttcatgg agcatgtcga ggagctcatc     180
gataccaaga tcgagggcta cgccaagaac aaggccctgt ccgagctggc cggtatccag     240
cgtaacctgg agacctacat ccagctgagg aacgagtggg agaacgatat cgagaactcc     300
aaggcccagg gcaaggtcgc taactactac gagagcctgg agcaggccgt cgagcgttca     360
atgcctcagt cgccgttga gaacttcgag gtcccttgc tgaccgtcta cgtccaggct      420
gctaacctcc atctcctgct cctcagggat gtcagcgttt acggcaagtg ctggggttgg     480
tctgagcaga agatcaagat ctactacgat aagcagatca agtacaccca tgagtacacc     540
aaccattgcg tcaactggta caacaagggc ctggagcgcc tgaagaacaa gggctcaagc     600
taccaggatt ggtacaacta caaccgcttc cgccgcgaga tgaccctgac cgtcctcgat     660
atcgtcgccc tgttccccca ttacgatgtc cagacctacc ccatcaccac cgtcgcccag     720
ctcacccgcg aggtctacac tgatcccctc ctgaacttca cccccaagct ccattcagtc     780
agccagctgc ccagcttcag cgatatggag aacgccacca tccgcacccc catctgatg     840
gagttcctgc gcatgctgac catctacacc gattggtaca gcgtcggccg caactactac     900
tggggcggcc atcgcgtcac ctcataccat gtcggcggcg agaacatccg ctctcctctg     960
tacggtaggg aggctaacca ggaggtccct agggatttct acttctacgg ccccgtcttc    1020
aagaccctgt ccaagcccac cctgaggcct ttgcagcagc tgctcctgc tcctcctttc    1080
aacttgcgtt ctctggaggg tgttgagttc atacccccca ccggttcatt catgtaccgc    1140
gagcgcggtt ctgtcgatag cttcaacgag ctgccccctt tcaacccggt cggtttgcct    1200
cataaggtct acagccatcg cctgtgccat gccaccttcg tccgtaagag cggcaccct    1260
```

-continued

```
tacctgacca ccggtgctat cttctcctgg acccataggt ccgctgagga gactaacacc    1320
atcgagtcaa acatcatcac ccagatcccc ctcgtcaagg cctaccagat cggcagcggc    1380
accaccgtcc gtaagggtcc tggtttcacc ggtggtgata tcctcaggcg taccggtcct    1440
ggtactttcg gtgatatgag gatcaacatc aacgccccc tctcccagag gtacagggtc     1500
cgtatccgtt acgcctctac caccgatctg cagttcgtca cctcaatcaa cggcaccacc    1560
atcaacatcg caacttccc caagaccatc aacaacctga caccctggg ctccgagggc      1620 taccgcaccg tctctttctc caccccttc agcttctcta acgcccagtc catcttccgc     1680
ctcggtatcc aggctttcag cggtgtccag gaggtttacg tcgataagat cgagttcatc    1740
cccgtcgagt ga                                                        1752
```

<210> SEQ ID NO 13
<211> LENGTH: 583
<212> TYPE: PRT
<213> ORGANISM: Artificial Sequence
<220> FEATURE:
<223> OTHER INFORMATION: variant AXMI-004B-3M sequence (AXMI-004B-3M-ALT2)

<400> SEQUENCE: 13

```
Met Ala Ala Met Glu Arg Phe Asp Lys Asn Asp Ala Leu Glu Ile Gly
 1               5                  10                  15

Met Ser Ile Val Ser Glu Leu Ile Gly Met Ile Pro Gly Gly Thr Ala
            20                  25                  30

Leu Gln Phe Val Phe Asn Gln Leu Trp Ser Arg Leu Gly Asp Ser Gly
        35                  40                  45

Trp Asn Ala Phe Met Glu His Val Glu Glu Leu Ile Asp Thr Lys Ile
    50                  55                  60

Glu Gly Tyr Ala Lys Asn Lys Ala Leu Ser Glu Leu Ala Gly Ile Gln
65                  70                  75                  80

Arg Asn Leu Glu Thr Tyr Ile Gln Leu Arg Asn Glu Trp Glu Asn Asp
                85                  90                  95

Ile Glu Asn Ser Lys Ala Gln Gly Lys Val Ala Asn Tyr Tyr Glu Ser
            100                 105                 110

Leu Glu Gln Ala Val Glu Arg Ser Met Pro Gln Phe Ala Val Glu Asn
        115                 120                 125

Phe Glu Val Pro Leu Leu Thr Val Tyr Val Gln Ala Ala Asn Leu His
    130                 135                 140

Leu Leu Leu Leu Arg Asp Val Ser Val Tyr Gly Lys Cys Trp Gly Trp
145                 150                 155                 160

Ser Glu Gln Lys Ile Lys Ile Tyr Tyr Asp Lys Gln Ile Lys Tyr Thr
                165                 170                 175

His Glu Tyr Thr Asn His Cys Val Asn Trp Tyr Asn Lys Gly Leu Glu
            180                 185                 190

Arg Leu Lys Asn Lys Gly Ser Ser Tyr Gln Asp Trp Tyr Asn Tyr Asn
        195                 200                 205

Arg Phe Arg Arg Glu Met Thr Leu Thr Val Leu Asp Ile Val Ala Leu
    210                 215                 220

Phe Pro His Tyr Asp Val Gln Thr Tyr Pro Ile Thr Thr Val Ala Gln
225                 230                 235                 240

Leu Thr Arg Glu Val Tyr Thr Asp Pro Leu Leu Asn Phe Asn Pro Lys
                245                 250                 255

Leu His Ser Val Ser Gln Leu Pro Ser Phe Ser Asp Met Glu Asn Ala
            260                 265                 270
```

```
Thr Ile Arg Thr Pro His Leu Met Glu Phe Leu Arg Met Leu Thr Ile
    275                 280                 285
Tyr Thr Asp Trp Tyr Ser Val Gly Arg Asn Tyr Tyr Trp Gly Gly His
290                 295                 300
Arg Val Thr Ser Tyr His Val Gly Gly Glu Asn Ile Arg Ser Pro Leu
305                 310                 315                 320
Tyr Gly Arg Glu Ala Asn Gln Glu Val Pro Arg Asp Phe Tyr Phe Tyr
                325                 330                 335
Gly Pro Val Phe Lys Thr Leu Ser Lys Pro Thr Leu Arg Pro Leu Gln
            340                 345                 350
Gln Pro Ala Pro Ala Pro Pro Phe Asn Leu Arg Ser Leu Glu Gly Val
        355                 360                 365
Glu Phe His Thr Pro Thr Gly Ser Phe Met Tyr Arg Glu Arg Gly Ser
370                 375                 380
Val Asp Ser Phe Asn Glu Leu Pro Pro Phe Asn Pro Val Gly Leu Pro
385                 390                 395                 400
His Lys Val Tyr Ser His Arg Leu Cys His Ala Thr Phe Val Arg Lys
                405                 410                 415
Ser Gly Thr Pro Tyr Leu Thr Thr Gly Ala Ile Phe Ser Trp Thr His
            420                 425                 430
Arg Ser Ala Glu Glu Thr Asn Thr Ile Glu Ser Asn Ile Ile Thr Gln
        435                 440                 445
Ile Pro Leu Val Lys Ala Tyr Gln Ile Gly Ser Gly Thr Thr Val Arg
    450                 455                 460
Lys Gly Pro Gly Phe Thr Gly Gly Asp Ile Leu Arg Arg Thr Gly Pro
465                 470                 475                 480
Gly Thr Phe Gly Asp Met Arg Ile Asn Ile Asn Ala Pro Leu Ser Gln
                485                 490                 495
Arg Tyr Arg Val Arg Ile Arg Tyr Ala Ser Thr Thr Asp Leu Gln Phe
            500                 505                 510
Val Thr Ser Ile Asn Gly Thr Thr Ile Asn Ile Gly Asn Phe Pro Lys
        515                 520                 525
Thr Ile Asn Asn Leu Asn Thr Leu Gly Ser Gly Tyr Arg Thr Val
    530                 535                 540
Ser Phe Ser Thr Pro Phe Ser Phe Ser Asn Ala Gln Ser Ile Phe Arg
545                 550                 555                 560
Leu Gly Ile Gln Ala Phe Ser Gly Val Gln Glu Val Tyr Val Asp Lys
                565                 570                 575
Ile Glu Phe Ile Pro Val Glu
            580
```

<210> SEQ ID NO 14
<211> LENGTH: 1752
<212> TYPE: DNA
<213> ORGANISM: Artificial Sequence
<220> FEATURE:
<223> OTHER INFORMATION: synthetic nucleotide sequence encoding
      AXMI-004B-3M-ALT3 (synaxmi-004B-3m-alt3)

<400> SEQUENCE: 14

```
atgcagatca tggagcgctt cgataagaac gatgccctcg agatcggcat gtccatcgtc    60
tccgagctca tcggcatgat ccccggcggc accgccctgc agttcgtctt caaccagctc   120
tggagccgcc tcggcgactc aggctggaac gctttcatgg agcatgtcga ggagctcatc   180
gataccaaga tcgagggcta cgccaagaac aaggccctgt ccgagctggc cgtataccag   240
cgtaacctgg agacctacat ccagctgagg aacgagtggg agaacgatat cgagaactcc   300
```

-continued

```
aaggcccagg gcaaggtcgc taactactac gagagcctgg agcaggccgt cgagcgttca    360
atgcctcagt tcgccgttga gaacttcgag gtccccttgc tgaccgtcta cgtccaggct    420
gctaacctcc atctcctgct cctcagggat gtcagcgttt acggcaagtg ctggggttgg    480
tctgagcaga agatcaagat ctactacgat aagcagatca agtacaccca tgagtacacc    540
aaccattgcg tcaactggta caacaagggc ctggagcgcc tgaagaacaa gggctcaagc    600
taccaggatt ggtacaacta caaccgcttc cgccgcgaga tgaccctgac cgtcctcgat    660
atcgtcgccc tgttccccca ttacgatgtc cagacctacc ccatcaccac cgtcgcccag    720
ctcacccgcg aggtctacac tgatccctc ctgaacttca cccccaagct ccattcagtc    780
agccagctgc ccagcttcag cgatatggag aacgccacca ccgcaccccc catctgatg    840
gagttcctgc gcatgctgac catctacacc gattggtaca gcgtcggccg caactactac    900
tggggcggcc atcgcgtcac ctcataccat gtcggcggcg agaacatccg ctctcctctg    960
tacggtaggg aggctaacca ggaggtccct agggatttct acttctacgg ccccgtcttc    1020
aagaccctgt ccaagcccac cctgaggcct ttgcagcagc ctgctcctgc tcctcctttc    1080
aacttgcgtt ctctggaggg tgttgagttc catacccca ccggttcatt catgtaccgc    1140
gagcgcggtt ctgtcgatag cttcaacgag ctgccccctt tcaacccgt cggtttgcct    1200
cataaggtct acagccatcg cctgtgccat gccaccttcg tccgtaagag cggcacccct    1260
tacctgacca ccggtgctat cttctcctgg acccataggt ccgctgagga gactaacacc    1320
atcgagtcaa acatcatcac ccagatcccc ctcgtcaagg cctaccagat cggcagcggc    1380
accaccgtcc gtaagggtcc tggtttcacc ggtggtgata tcctcaggcg taccggtcct    1440
ggtactttcg gtgatatgag gatcaacatc aacgccccc tctcccagag gtacagggtc    1500
cgtatccgtt acgcctctac caccgatctg cagttcgtca cctcaatcaa cggcaccacc    1560
atcaacatcg gcaacttccc caagaccatc aacaacctga caccctgggg ctccgagggc    1620
taccgcaccg tctctttctc cacccctttc agcttctcta acgcccagtc catcttccgc    1680
ctcggtatcc aggctttcag cggtgtccag gaggtttacg tcgataagat cgagttcatc    1740
cccgtcgagt ga                                                        1752
```

<210> SEQ ID NO 15
<211> LENGTH: 583
<212> TYPE: PRT
<213> ORGANISM: Artificial Sequence
<220> FEATURE:
<223> OTHER INFORMATION: variant AXMI-004B-3M sequence (AXMI-004B-3M-ALT3)

<400> SEQUENCE: 15

```
Met Gln Ile Met Glu Arg Phe Asp Lys Asn Asp Ala Leu Glu Ile Gly
  1               5                  10                  15

Met Ser Ile Val Ser Glu Leu Ile Gly Met Ile Pro Gly Gly Thr Ala
             20                  25                  30

Leu Gln Phe Val Phe Asn Gln Leu Trp Ser Arg Leu Gly Asp Ser Gly
         35                  40                  45

Trp Asn Ala Phe Met Glu His Val Glu Glu Leu Ile Asp Thr Lys Ile
     50                  55                  60

Glu Gly Tyr Ala Lys Asn Lys Ala Leu Ser Glu Leu Ala Gly Ile Gln
 65                  70                  75                  80

Arg Asn Leu Glu Thr Tyr Ile Gln Leu Arg Asn Glu Trp Glu Asn Asp
                 85                  90                  95
```

```
Ile Glu Asn Ser Lys Ala Gln Gly Lys Val Ala Asn Tyr Tyr Glu Ser
            100                 105                 110

Leu Glu Gln Ala Val Glu Arg Ser Met Pro Gln Phe Ala Val Glu Asn
            115                 120                 125

Phe Glu Val Pro Leu Leu Thr Val Tyr Val Gln Ala Ala Asn Leu His
            130                 135                 140

Leu Leu Leu Leu Arg Asp Val Ser Val Tyr Gly Lys Cys Trp Gly Trp
145                 150                 155                 160

Ser Glu Gln Lys Ile Lys Ile Tyr Tyr Asp Lys Gln Ile Lys Tyr Thr
                165                 170                 175

His Glu Tyr Thr Asn His Cys Val Asn Trp Tyr Asn Lys Gly Leu Glu
            180                 185                 190

Arg Leu Lys Asn Lys Gly Ser Ser Tyr Gln Asp Trp Tyr Asn Tyr Asn
            195                 200                 205

Arg Phe Arg Arg Glu Met Thr Leu Thr Val Leu Asp Ile Val Ala Leu
            210                 215                 220

Phe Pro His Tyr Asp Val Gln Thr Tyr Pro Ile Thr Thr Val Ala Gln
225                 230                 235                 240

Leu Thr Arg Glu Val Tyr Thr Asp Pro Leu Leu Asn Phe Asn Pro Lys
                245                 250                 255

Leu His Ser Val Ser Gln Leu Pro Ser Phe Ser Asp Met Glu Asn Ala
            260                 265                 270

Thr Ile Arg Thr Pro His Leu Met Glu Phe Leu Arg Met Leu Thr Ile
            275                 280                 285

Tyr Thr Asp Trp Tyr Ser Val Gly Arg Asn Tyr Tyr Trp Gly His
            290                 295                 300

Arg Val Thr Ser Tyr His Val Gly Gly Glu Asn Ile Arg Ser Pro Leu
305                 310                 315                 320

Tyr Gly Arg Glu Ala Asn Gln Glu Val Pro Arg Asp Phe Tyr Phe Tyr
                325                 330                 335

Gly Pro Val Phe Lys Thr Leu Ser Lys Pro Thr Leu Arg Pro Leu Gln
            340                 345                 350

Gln Pro Ala Pro Ala Pro Pro Phe Asn Leu Arg Ser Leu Glu Gly Val
            355                 360                 365

Glu Phe His Thr Pro Thr Gly Ser Phe Met Tyr Arg Glu Arg Gly Ser
            370                 375                 380

Val Asp Ser Phe Asn Glu Leu Pro Pro Phe Asn Pro Val Gly Leu Pro
385                 390                 395                 400

His Lys Val Tyr Ser His Arg Leu Cys His Ala Thr Phe Val Arg Lys
                405                 410                 415

Ser Gly Thr Pro Tyr Leu Thr Thr Gly Ala Ile Phe Ser Trp Thr His
            420                 425                 430

Arg Ser Ala Glu Glu Thr Asn Thr Ile Glu Ser Asn Ile Ile Thr Gln
            435                 440                 445

Ile Pro Leu Val Lys Ala Tyr Gln Ile Gly Ser Gly Thr Thr Val Arg
            450                 455                 460

Lys Gly Pro Gly Phe Thr Gly Gly Asp Ile Leu Arg Arg Thr Gly Pro
465                 470                 475                 480

Gly Thr Phe Gly Asp Met Arg Ile Asn Ile Asn Ala Pro Leu Ser Gln
                485                 490                 495

Arg Tyr Arg Val Arg Ile Arg Tyr Ala Ser Thr Thr Asp Leu Gln Phe
            500                 505                 510

Val Thr Ser Ile Asn Gly Thr Thr Ile Asn Ile Gly Asn Phe Pro Lys
            515                 520                 525
```

-continued

```
Thr Ile Asn Asn Leu Asn Thr Leu Gly Ser Glu Gly Tyr Arg Thr Val
    530                 535                 540

Ser Phe Ser Thr Pro Phe Ser Phe Ser Asn Ala Gln Ser Ile Phe Arg
545                 550                 555                 560

Leu Gly Ile Gln Ala Phe Ser Gly Val Gln Glu Val Tyr Val Asp Lys
                565                 570                 575

Ile Glu Phe Ile Pro Val Glu
            580

<210> SEQ ID NO 16
<211> LENGTH: 1743
<212> TYPE: DNA
<213> ORGANISM: Bacillus thuringiensis

<400> SEQUENCE: 16
atggaacggt ttgataagaa tgatgcactg gaaattggta tgtccattgt atctgaactt      60
attggtatga ttccaggcgg aacagctttg caatttgtgt ttaatcaatt gtggtctcgt     120
ttaggtgatt ctggatggaa tgcgttcatg gaacatgtgg aggaattaat tgatactaaa     180
atagaagggt atgcaaaaaa taaagcctta tctgaattag caggtataca aagaaacctt     240
gaaacatata tacaattacg taatgaatgg gaaaatgata ttgaaaactc aaaggctcaa     300
ggtaaggtag ctaattacta tgaaagtctt gagcaggcgg ttgaaaggag tatgcctcaa     360
tttgcagtgg agaattttga agtaccactt ttaactgtct atgtgcaagc tgctaatctt     420
catttattat tattaagaga tgtttcagtt tatggaaagt gttggggatg gtcggagcag     480
aaaattaaaa tttattatga taaacagatt aagtataccc atgaatacac aaatcattgt     540
gtaaattggt ataataaagg acttgagaga ttaaaaaata aaggttcttc ttatcaagat     600
tggtacaatt ataatcgttt ccgtagagaa atgactctta ctgttttaga tatcgttgct     660
ttattcccgc actatgatgt acaaacttat ccaataacaa ccgttgctca gctaacaagg     720
gaagtttata cggatccttt acttaatttt aatcctaaat tacattctgt gtctcaatta     780
cctagtttta gtgacatgga aaatgcaaca attagaactc cacatctgat ggaatttttta     840 agaatgctaa caatttatac agattggtat agtgtgggaa gaaactatta ttggggagga     900
catcgcgtga cgtcttacca tgtaggagga gagaatataa gatcacctct atatggtaga     960
gaggcaaatc aagaggttcc tagagatttt tatttttatg gacccgtttt taagacgtta    1020
tcaaagccga ctctaagacc attacagcag cctgcaccag ctcctccttt taatttacgt    1080
agcttagagg gagtagaatt ccacactcct acaggtagtt ttatgtatcg tgaaagagga    1140
tcggtagatt cttttaatga gttgccgcct tttaatccag ttgggttacc tcataaggta    1200
tacagtcacc gtttatgtca tgcaacgttt gttcgtaaat ctgggacccc ttatttaaca    1260
acaggtgcca tcttttcttg gacacatcgt agtgctgaag aaaccaatac aattgaatca    1320
aatattatta cgcaaatccc gttagtaaaa gcatatcaaa ttgggtcagg cactactgta    1380
aggaaaggac caggattcac aggaggggat atacttcgaa gaacaggtcc tggaacattt    1440
ggagatatga gaataaatat taatgcacca ttatctcaaa gatatcgtgt aaggattcgt    1500
tatgcttcta cgacagattt acaatttgtc acgagtatta atgggaccac cattaatatt    1560
ggtaacttcc cgaaaactat taataatcta aatactttag gttctgaggg ctatagaaca    1620
gtatcgttta gtactccatt tagtttctca aatgcacaaa gcatatttag attaggtata    1680
caagcatttt ctggagttca agaagtttat gtggataaaa ttgaatttat tcctgttgaa    1740
tag                                                                  1743
```

<210> SEQ ID NO 17
<211> LENGTH: 1749
<212> TYPE: DNA
<213> ORGANISM: Artificial Sequence
<220> FEATURE:
<223> OTHER INFORMATION: synthetic nucleotide sequence encoding
      AXMI-004B-3M-ALT4 (synaxmi-004B-3m-alt4)

<400> SEQUENCE: 17

```
atggcggcgg agagatttga caagaatgat gctctggaga ttgggatgag catcgtctcc      60
gagctgattg gatgattcc tggagggacg gcgctgcaat ttgtcttcaa tcagctgtgg     120
tcaaggctgg agattctgg atggaatgcc ttcatggagc atgtggagga gctcatcgac     180
accaagattg aaggatatgc caagaacaag gcgctctcag agctggccgg catccagagg     240
aacctggaga cctacatcca gctgaggaat gaatgggaga tgacatcga aacagcaag     300
gctcaaggca aggtggccaa ctactacgag agcttggagc aagctgttga agatcaatg     360
cctcaatttg ctgtggagaa cttcgaggtg ccgctgctca ccgtctatgt tcaagctgcc     420
aacctccacc tgctgctgct gagagatgtt tcagtttatg gaaatgctg gggctggagc     480
gagcagaaga tcaagatcta ctacgacaag cagatcaagt acacccatga gtacaccaac     540
cactgcgtca actggtacaa caaggggctg gagaggctga agaacaaggg ctcaagctac     600
caagattggt acaactacaa caggttcaga agggagatga cattgacggt gctggacatc     660
gtggcgctct ccctcatta tgatgttcaa acctacccca tcaccaccgt ggcgcagctg     720
acaagagaag tctacaccga cccgctgcta aacttcaacc ccaagctgca ttctgtgagc     780
cagctgccga gcttctccga catggagaat gccaccatca ggacgccgca cctgatggag     840
ttcttgagga tgctcaccat ctacactgat tggtattctg ttggaaggaa ctactactgg     900
ggcggccacc gcgtcacctc atatcatgtt ggtggtgaga acatccgctc gccgctctat     960
ggaagagaag caaatcaaga agttccaaga gatttctact tctatggacc tgtcttcaag    1020
accttgtcaa agccaacatt gaggccgctc cagcagccgg cgccggcgcc gcccttcaac    1080
ctgaggagct tggaaggagt tgagttccac acgccaactg gcagcttcat gtacagagaa    1140
agaggatcag tggacagctt caacgagctg ccgccttca accctgttgg gctgccgcac    1200
aaggtctaca gccaccgcct ctgccatgcc accttcgtga ggaagagcgg cacgccgtac    1260
ctcaccaccg gcgccatctt ctcatggacc caccgctctg ctgaagaaac caacaccatc    1320
gagagcaaca tcatcaccca gatcccgctg gtgaaggcct accagattgg atcaggcacc    1380
accgtgagga aaggacctgg cttcactgga ggagacatct tgaggaggac tggacctgga    1440
acatttggag acatgaggat caacatcaac gcgccgctga gccaaagata cagggtgagg    1500
atcagatatg cttcaacaac tgatcttcaa tttgtgacaa gcatcaatgg caccaccatc    1560
aacatcggca cttcccccaa gaccatcaac aacctcaaca ccttgggctc agaaggctac    1620
aggacggtga gcttctccac gcccttcagc ttcagcaatg ctcaaagcat cttccgcctc    1680
ggcatccaag ccttctctgg agttcaagaa gtttatgtgg acaagattga gttcatcccg    1740
gtggagtaa                                                             1749
```

<210> SEQ ID NO 18
<211> LENGTH: 582
<212> TYPE: PRT
<213> ORGANISM: Artificial Sequence
<220> FEATURE:
<223> OTHER INFORMATION: variant AXMI-004B-3M sequence (AXMI-004B-3M-
      ALT4)

<400> SEQUENCE: 18

```
Met Ala Ala Glu Arg Phe Asp Lys Asn Asp Ala Leu Glu Ile Gly Met
 1               5                  10                  15

Ser Ile Val Ser Glu Leu Ile Gly Met Ile Pro Gly Gly Thr Ala Leu
             20                  25                  30

Gln Phe Val Phe Asn Gln Leu Trp Ser Arg Leu Gly Asp Ser Gly Trp
         35                  40                  45

Asn Ala Phe Met Glu His Val Glu Glu Leu Ile Asp Thr Lys Ile Glu
     50                  55                  60

Gly Tyr Ala Lys Asn Lys Ala Leu Ser Glu Leu Ala Gly Ile Gln Arg
 65                  70                  75                  80

Asn Leu Glu Thr Tyr Ile Gln Leu Arg Asn Glu Trp Glu Asn Asp Ile
                 85                  90                  95

Glu Asn Ser Lys Ala Gln Gly Lys Val Ala Asn Tyr Tyr Glu Ser Leu
            100                 105                 110

Glu Gln Ala Val Glu Arg Ser Met Pro Gln Phe Ala Val Glu Asn Phe
        115                 120                 125

Glu Val Pro Leu Leu Thr Val Tyr Val Gln Ala Ala Asn Leu His Leu
    130                 135                 140

Leu Leu Leu Arg Asp Val Ser Val Tyr Gly Lys Cys Trp Gly Trp Ser
145                 150                 155                 160

Glu Gln Lys Ile Lys Ile Tyr Tyr Asp Lys Gln Ile Lys Tyr Thr His
                165                 170                 175

Glu Tyr Thr Asn His Cys Val Asn Trp Tyr Asn Lys Gly Leu Glu Arg
            180                 185                 190

Leu Lys Asn Lys Gly Ser Ser Tyr Gln Asp Trp Tyr Asn Tyr Asn Arg
        195                 200                 205

Phe Arg Arg Glu Met Thr Leu Thr Val Leu Asp Ile Val Ala Leu Phe
    210                 215                 220

Pro His Tyr Asp Val Gln Thr Tyr Pro Ile Thr Thr Val Ala Gln Leu
225                 230                 235                 240

Thr Arg Glu Val Tyr Thr Asp Pro Leu Leu Asn Phe Asn Pro Lys Leu
                245                 250                 255

His Ser Val Ser Gln Leu Pro Ser Phe Ser Asp Met Glu Asn Ala Thr
            260                 265                 270

Ile Arg Thr Pro His Leu Met Glu Phe Leu Arg Met Leu Thr Ile Tyr
        275                 280                 285

Thr Asp Trp Tyr Ser Val Gly Arg Asn Tyr Tyr Trp Gly Gly His Arg
    290                 295                 300

Val Thr Ser Tyr His Val Gly Gly Glu Asn Ile Arg Ser Pro Leu Tyr
305                 310                 315                 320

Gly Arg Glu Ala Asn Gln Glu Val Pro Arg Asp Phe Tyr Phe Tyr Gly
                325                 330                 335

Pro Val Phe Lys Thr Leu Ser Lys Pro Thr Leu Arg Pro Leu Gln Gln
            340                 345                 350

Pro Ala Pro Ala Pro Phe Asn Leu Arg Ser Leu Glu Gly Val Glu
        355                 360                 365

Phe His Thr Pro Thr Gly Ser Phe Met Tyr Arg Glu Arg Gly Ser Val
    370                 375                 380

Asp Ser Phe Asn Glu Leu Pro Pro Phe Asn Pro Val Gly Leu Pro His
385                 390                 395                 400

Lys Val Tyr Ser His Arg Leu Cys His Ala Thr Phe Val Arg Lys Ser
                405                 410                 415
```

-continued

```
Gly Thr Pro Tyr Leu Thr Thr Gly Ala Ile Phe Ser Trp Thr His Arg
            420                 425                 430

Ser Ala Glu Glu Thr Asn Thr Ile Glu Ser Asn Ile Ile Thr Gln Ile
        435                 440                 445

Pro Leu Val Lys Ala Tyr Gln Ile Gly Ser Gly Thr Thr Val Arg Lys
        450                 455                 460

Gly Pro Gly Phe Thr Gly Gly Asp Ile Leu Arg Arg Thr Gly Pro Gly
465                 470                 475                 480

Thr Phe Gly Asp Met Arg Ile Asn Ile Asn Ala Pro Leu Ser Gln Arg
                485                 490                 495

Tyr Arg Val Arg Ile Arg Tyr Ala Ser Thr Thr Asp Leu Gln Phe Val
            500                 505                 510

Thr Ser Ile Asn Gly Thr Thr Ile Asn Ile Gly Asn Phe Pro Lys Thr
            515                 520                 525

Ile Asn Asn Leu Asn Thr Leu Gly Ser Glu Gly Tyr Arg Thr Val Ser
        530                 535                 540

Phe Ser Thr Pro Phe Ser Phe Ser Asn Ala Gln Ser Ile Phe Arg Leu
545                 550                 555                 560

Gly Ile Gln Ala Phe Ser Gly Val Gln Glu Val Tyr Val Asp Lys Ile
                565                 570                 575

Glu Phe Ile Pro Val Glu
            580
```

SYNTHETIC AXMI-004 DELTA-ENDOTOXIN GENES AND METHODS FOR THEIR USE

CROSS-REFERENCE TO RELATED APPLICATIONS

This application claims the benefit of U.S. Provisional Application No. 60/972,546, filed Sep. 14, 2007, which is hereby incorporated in its entirety by reference herein.

REFERENCE TO SEQUENCE LISTING SUBMITTED ELECTRONICALLY

The official copy of the sequence listing is submitted electronically via EFS-Web as an ASCII formatted sequence listing with a file named "362196_SequenceListing.txt", created on Sep. 8, 2008, and having a size of 60 kilobytes and is filed concurrently with the specification. The sequence listing contained in this ASCII formatted document is part of the specification and is herein incorporated by reference in its entirety.

FIELD OF THE INVENTION

This invention relates to the field of molecular biology. Provided are novel genes that encode pesticidal proteins. These proteins and the nucleic acid sequences that encode them are useful in preparing pesticidal formulations and in the production of transgenic pest-resistant plants.

BACKGROUND OF THE INVENTION

*Bacillus thuringiensis* is a Gram-positive spore forming soil bacterium characterized by its ability to produce crystalline inclusions that are specifically toxic to certain orders and species of insects, but are harmless to plants and other non-targeted organisms. For this reason, compositions including *Bacillus thuringiensis* strains or their insecticidal proteins can be used as environmentally-acceptable insecticides to control agricultural insect pests or insect vectors for a variety of human or animal diseases.

Crystal (Cry) proteins (delta-endotoxins) from *Bacillus thuringiensis* have potent insecticidal activity against predominantly Lepidopteran, Dipteran, and Coleopteran larvae. These proteins also have shown activity against Hymenoptera, Homoptera, Phthiraptera, Mallophaga, and Acari pest orders, as well as other invertebrate orders such as Nemathelminthes, Platyhelminthes, and Sarcomastigorphora (Feitelson (1993) The Bacillus Thuringiensis family tree. In *Advanced Engineered Pesticides*, Marcel Dekker, Inc., New York, N.Y.) These proteins were originally classified as CryI to CryV based primarily on their insecticidal activity. The major classes were Lepidoptera-specific (I), Lepidoptera- and Diptera-specific (TI), Coleoptera-specific (III), Diptera-specific (IV), and nematode-specific (V) and (VI). The proteins were further classified into subfamilies; more highly related proteins within each family were assigned divisional letters such as Cry1A, Cry1B, Cry1C, etc. Even more closely related proteins within each division were given names such as Cry1C1, Cry1C2, etc.

A new nomenclature was recently described for the Cry genes based upon amino acid sequence homology rather than insect target specificity (Crickmore et al. (1998) *Microbiol. Mol. Biol. Rev.* 62:807-813). In the new classification, each toxin is assigned a unique name incorporating a primary rank (an Arabic number), a secondary rank (an uppercase letter), a tertiary rank (a lowercase letter), and a quaternary rank (another Arabic number). In the new classification, Roman numerals have been exchanged for Arabic numerals in the primary rank. Proteins with less than 45% sequence identity have different primary ranks, and the criteria for secondary and tertiary ranks are 78% and 95%, respectively.

The crystal protein does not exhibit insecticidal activity until it has been ingested and solubilized in the insect midgut. The ingested protoxin is hydrolyzed by proteases in the insect digestive tract to an active toxic molecule. (Höfte and Whiteley (1989) *Microbiol. Rev.* 53:242-255). This toxin binds to apical brush border receptors in the midgut of the target larvae and inserts into the apical membrane creating ion channels or pores, resulting in larval death.

Delta-endotoxins generally have five conserved sequence domains, and three conserved structural domains (see, for example, de Maagd et al. (2001) *Trends Genetics* 17:193-199). The first conserved structural domain consists of seven alpha helices and is involved in membrane insertion and pore formation. Domain II consists of three beta-sheets arranged in a Greek key configuration, and domain III consists of two antiparallel beta-sheets in "jelly-roll" formation (de Maagd et al., 2001, supra). Domains II and III are involved in receptor recognition and binding, and are therefore considered determinants of toxin specificity.

Because of the devastation that insects can confer there is a continual need to discover new forms of *Bacillus thuringiensis* delta-endotoxins.

SUMMARY OF INVENTION

Compositions and methods for conferring pest resistance to bacteria, plants, plant cells, tissues and seeds are provided. Compositions include nucleic acid molecules encoding sequences for delta-endotoxin polypeptides, vectors comprising those nucleic acid molecules, and host cells comprising the vectors. Compositions also include the polypeptide sequences of the endotoxin, and antibodies to those polypeptides. The nucleotide sequences can be used in DNA constructs or expression cassettes for transformation and expression in organisms, including microorganisms and plants. The nucleotide or amino acid sequences may be synthetic sequences that have been designed for expression in an organism including, but not limited to, a microorganism or a plant. Compositions also comprise transformed bacteria, plants, plant cells, tissues, and seeds.

In particular, isolated nucleic acid molecules corresponding to delta-endotoxin nucleic acid sequences are provided. Additionally, amino acid sequences corresponding to the polynucleotides are encompassed. In particular, the present invention provides for an isolated nucleic acid molecule comprising a nucleotide sequence encoding the amino acid sequence shown in SEQ ID NO:9, 11, 13, 15, or 18, or a nucleotide sequence set forth in SEQ ID NO:1, 2, 4, 6, 7, 8, 10, 12, 14, 16, or 17, as well as variants and fragments thereof. Nucleotide sequences that are complementary to a nucleotide sequence of the invention, or that hybridize to a sequence of the invention are also encompassed.

Methods are provided for producing the polypeptides of the invention, and for using those polypeptides for controlling or killing a lepidopteran or coleopteran pest. Methods and kits for detecting the nucleic acids and polypeptides of the invention in a sample are also included.

The compositions and methods of the invention are useful for the production of organisms with pesticide resistance, specifically bacteria and plants. These organisms and compositions derived from them are desirable for agricultural purposes. The compositions of the invention are also useful for generating altered or improved delta-endotoxin proteins that have pesticidal activity, or for detecting the presence of delta-endotoxin proteins or nucleic acids in products or organisms.

DESCRIPTION OF FIGURES

FIGS. 1A and 1B show an alignment of AXMI-004 (SEQ ID NO:3) with AXMI-004B-2M (SEQ ID NO:5), AXMI-004B-3M (SEQ ID NO:9), AXMI-004B-3M-ALT1 (SEQ ID NO:11), AXMI-004B-3M-ALT2 (SEQ ID NO:13), and AXMI-004B-3M-ALT3 (SEQ ID NO:15).

DETAILED DESCRIPTION

The present invention is drawn to compositions and methods for regulating pest resistance in organisms, particularly plants or plant cells. The methods involve transforming organisms with a nucleotide sequence encoding a delta-endotoxin protein of the invention. In particular, the nucleotide sequences of the invention are useful for preparing plants and microorganisms that possess pesticidal activity. Thus, transformed bacteria, plants, plant cells, plant tissues and seeds are provided. Compositions are delta-endotoxin nucleic acids and proteins of *Bacillus thuringiensis*. The sequences find use in the construction of expression vectors for subsequent transformation into organisms of interest, as probes for the isolation of other delta-endotoxin genes, and for the generation of altered pesticidal proteins by methods known in the art, such as domain swapping or DNA shuffling. The proteins find use in controlling or killing lepidopteran, coleopteran, and nematode pest populations, and for producing compositions with pesticidal activity.

By "delta-endotoxin" is intended a toxin from *Bacillus thuringiensis* that has toxic activity against one or more pests, including, but not limited to, members of the Lepidoptera, Diptera, and Coleoptera orders or members of the Nematoda phylum, or a protein that has homology to such a protein. In some cases, delta-endotoxin proteins have been isolated from other organisms, including *Clostridium bifermentans* and *Paenibacillus popilliae*. Delta-endotoxin proteins include amino acid sequences deduced from the full-length nucleotide sequences disclosed herein, and amino acid sequences that are shorter than the full-length sequences, either due to the use of an alternate downstream start site, or due to processing that produces a shorter protein having pesticidal activity. Processing may occur in the organism the protein is expressed in, or in the pest after ingestion of the protein. Delta-endotoxins include proteins identified as cry1 through cry43, cyt1 and cyt2, and Cyt-like toxin. There are currently over 250 known species of delta-endotoxins with a wide range of specificities and toxicities. For an expansive list see Crickmore et al. (1998), *Microbiol. Mol. Biol. Rev.* 62:807-813, and for regular updates see Crickmore et al. (2003) "*Bacillus thuringiensis* toxin nomenclature," at www.biols.susx.ac.uk/Home/Neil_Crickmore/Bt/index.

Provided herein are novel isolated nucleotide sequences that confer pesticidal activity. Also provided are the amino acid sequences of the delta-endotoxin proteins. The protein resulting from translation of this gene allows cells to control or kill pests that ingest it.

Isolated Nucleic Acid Molecules, and Variants and Fragments Thereof

One aspect of the invention pertains to isolated or recombinant nucleic acid molecules comprising nucleotide sequences encoding delta-endotoxin proteins and polypeptides or biologically active portions thereof, as well as nucleic acid molecules sufficient for use as hybridization probes to identify delta-endotoxin encoding nucleic acids. As used herein, the term "nucleic acid molecule" is intended to include DNA molecules (e.g., recombinant DNA, cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" or "purified" nucleic acid molecule or protein, or biologically active portion thereof, is substantially free of other cellular material, or culture medium when produced by recombinant techniques, or substantially free of chemical precursors or other chemicals when chemically synthesized. Preferably, an "isolated" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For purposes of the invention, "isolated" when used to refer to nucleic acid molecules excludes isolated chromosomes. For example, in various embodiments, the isolated delta-endotoxin encoding nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. A delta-endotoxin protein that is substantially free of cellular material includes preparations of protein having less than about 30%, 20%, 10%, or 5% (by dry weight) of non-delta-endotoxin protein (also referred to herein as a "contaminating protein").

Nucleotide sequences encoding the proteins of the present invention include the sequence set forth in SEQ ID NO:1, 2, 4, 6, 7, 8, 10, 12, 14, 16, or 17, and variants, fragments, and complements thereof. By "complement" is intended a nucleotide sequence that is sufficiently complementary to a given nucleotide sequence such that it can hybridize to the given nucleotide sequence to thereby form a stable duplex. The corresponding amino acid sequence for the delta-endotoxin protein encoded by this nucleotide sequence are set forth in SEQ ID NO:9, 11, 13, 15, or 18.

Nucleic acid molecules that are fragments of these delta-endotoxin encoding nucleotide sequences are also encompassed by the present invention (for example, SEQ ID NO:6 is a fragment of SEQ ID NO:4 and 10; SEQ ID NO:4 is a fragment of SEQ ID NO:2). By "fragment" is intended a portion of the nucleotide sequence encoding a delta-endotoxin protein. A fragment of a nucleotide sequence may encode a biologically active portion of a delta-endotoxin protein, or it may be a fragment that can be used as a hybridization probe or PCR primer using methods disclosed below. Nucleic acid molecules that are fragments of a delta-endotoxin nucleotide sequence comprise at least about 50, 100, 200, 300, 400, 500, 600, 700, 800, 900, 1000, 1050, 1100, 1150, 1200, 1250, 1300, 1350, 1400, 1450, 1500, 1550, 1600, 1650, 1700, 1750, 1800, 1850, 1860, 1870, 1880, 1885 contiguous nucleotides, or up to the number of nucleotides present in a full-length delta-endotoxin encoding nucleotide sequence disclosed herein (for example, 1890 nucleotides for SEQ ID NO:1 and 2, 1806 nucleotides for SEQ ID NO:4, 1743 nucleotides for SEQ ID NO:6, 7, 8, and 16, 1809 nucleotides for SEQ ID NO:10, and 1752 nucleotides for SEQ ID NO:12 and 14) depending upon the intended use. By "contiguous" nucleotides is intended nucleotide residues that are immediately adjacent to one another. Fragments of the nucleotide sequences of the present invention will encode protein fragments that retain the biological activity of the delta-endotoxin protein and, hence, retain pesticidal activity. By "retains activity" is intended that the fragment will have at least about 30%, at least about 50%, at least about 70%, 80%, 90%, 95% or higher of the pesticidal activity of the delta-endotoxin protein. Methods for measuring pesticidal activity are well known in the art. See, for example, Czapla and Lang (1990) *J. Econ. Entomol.* 83:2480-2485; Andrews et al. (1988) *Biochem. J.* 252:199-206; Marrone et al. (1985) *J. of Economic Entomology* 78:290-293; and U.S. Pat. No. 5,743,477, all of which are herein incorporated by reference in their entirety.

A fragment of a delta-endotoxin encoding nucleotide sequence that encodes a biologically active portion of a protein of the invention will encode at least about 15, 25, 30, 50, 75, 100, 125, 150, 175, 200, 250, 300, 350, 400, 450, 500, 550, 560, 570, 575, 580, 585, 590, 595, 600 contiguous amino acids, or up to the total number of amino acids present in a full-length delta-endotoxin protein of the invention (for example, 580 amino acids for SEQ ID NO:9, 602 amino acids for SEQ ID NO:11, and 583 amino acids for SEQ ID NO:13 and 15).

Preferred delta-endotoxin proteins of the present invention are encoded by a nucleotide sequence sufficiently identical to the nucleotide sequence of SEQ ID NO:1, 2, 4, 6, 7, 8, 10, 12, 14, 16, or 17. By "sufficiently identical" is intended an amino acid or nucleotide sequence that has at least about 60% or 65% sequence identity, about 70% or 75% sequence identity, about 80% or 85% sequence identity, about 90%, 91%, 92%, 93%, 94%, 95%, 96%, 97%, 98%, 99% or greater sequence identity compared to a reference sequence using one of the alignment programs described herein using standard parameters. One of skill in the art will recognize that these values can be appropriately adjusted to determine corresponding identity of proteins encoded by two nucleotide sequences by taking into account codon degeneracy, amino acid similarity, reading frame positioning, and the like.

To determine the percent identity of two amino acid sequences or of two nucleic acids, the sequences are aligned for optimal comparison purposes. The percent identity between the two sequences is a function of the number of identical positions shared by the sequences (i.e., percent identity=number of identical positions/total number of positions (e.g., overlapping positions)×100). In one embodiment, the two sequences are the same length. The percent identity between two sequences can be determined using techniques similar to those described below, with or without allowing gaps. In calculating percent identity, typically exact matches are counted.

The determination of percent identity between two sequences can be accomplished using a mathematical algorithm. A nonlimiting example of a mathematical algorithm utilized for the comparison of two sequences is the algorithm of Karlin and Altschul (1990) *Proc. Natl. Acad. Sci. USA* 87:2264, modified as in Karlin and Altschul (1993) *Proc. Natl. Acad. Sci. USA* 90:5873-5877. Such an algorithm is incorporated into the BLASTN and BLASTX programs of Altschul et al. (1990) *J. Mol. Biol.* 215:403. BLAST nucleotide searches can be performed with the BLASTN program, score=100, wordlength=12, to obtain nucleotide sequences homologous to delta-endotoxin-like nucleic acid molecules of the invention. BLAST protein searches can be performed with the BLASTX program, score=50, wordlength=3, to obtain amino acid sequences homologous to delta-endotoxin protein molecules of the invention. To obtain gapped alignments for comparison purposes, Gapped BLAST (in BLAST 2.0) can be utilized as described in Altschul et al. (1997) *Nucleic Acids Res.* 25:3389. Alternatively, PSI-Blast can be used to perform an iterated search that detects distant relationships between molecules. See Altschul et al. (1997) supra.

When utilizing BLAST, Gapped BLAST, and PSI-Blast programs, the default parameters of the respective programs (e.g., BLASTX and BLASTN) can be used. Alignment may also be performed manually by inspection.

Another non-limiting example of a mathematical algorithm utilized for the comparison of sequences is the ClustalW algorithm (Higgins et al. (1994) *Nucleic Acids Res.* 22:4673-4680). ClustalW compares sequences and aligns the entirety of the amino acid or DNA sequence, and thus can provide data about the sequence conservation of the entire amino acid sequence. The ClustalW algorithm is used in several commercially available DNA/amino acid analysis software packages, such as the ALIGNX module of the Vector NTI Program Suite (Invitrogen Corporation, Carlsbad, Calif.). After alignment of amino acid sequences with ClustalW, the percent amino acid identity can be assessed. A non-limiting example of a software program useful for analysis of ClustalW alignments is GENEDOC™. GENEDOC™ (Karl Nicholas) allows assessment of amino acid (or DNA) similarity and identity between multiple proteins. Another non-limiting example of a mathematical algorithm utilized for the comparison of sequences is the algorithm of Myers and Miller (1988) *CABIOS* 4: 11-17. Such an algorithm is incorporated into the ALIGN program (version 2.0), which is part of the GCG Wisconsin Genetics Software Package, Version 10 (available from Accelrys, Inc., 9685 Scranton Rd., San Diego, Calif., USA). When utilizing the ALIGN program for comparing amino acid sequences, a PAM120 weight residue table, a gap length penalty of 12, and a gap penalty of 4 can be used.

Unless otherwise stated, GAP Version 10, which uses the algorithm of Needleman and Wunsch (1970) *J. Mol. Biol.* 48(3):443-453, will be used to determine sequence identity or similarity using the following parameters: % identity and % similarity for a nucleotide sequence using GAP Weight of 50 and Length Weight of 3, and the nwsgapdna.cmp scoring matrix; % identity or % similarity for an amino acid sequence using GAP weight of 8 and length weight of 2, and the BLOSUM62 scoring program. Equivalent programs may also be used. By "equivalent program" is intended any sequence comparison program that, for any two sequences in question, generates an alignment having identical nucleotide residue matches and an identical percent sequence identity when compared to the corresponding alignment generated by GAP Version 10.

The invention also encompasses variant nucleic acid molecules (for example, SEQ ID NO:2 is a variant of SEQ ID NO:1; SEQ ID NO:7 and 8 are variants of SEQ ID NO:6; SEQ ID NO:10 is a variant of SEQ ID NO:4 and 12; and SEQ ID NO:14 is a variant of SEQ ID NO:12). "Variants" of the delta-endotoxin encoding nucleotide sequences include those sequences that encode the delta-endotoxin proteins disclosed herein but that differ conservatively because of the degeneracy of the genetic code as well as those that are sufficiently identical as discussed above. Naturally occurring allelic variants can be identified with the use of well-known molecular biology techniques, such as polymerase chain reaction (PCR) and hybridization techniques as outlined below. Variant nucleotide sequences also include synthetically derived nucleotide sequences that have been generated, for example, by using site-directed mutagenesis but which still encode the delta-endotoxin proteins disclosed in the present invention as discussed below. Variant proteins encompassed by the present invention are biologically active, that is they continue to possess the desired biological activity of the native protein, that is, retaining pesticidal activity. By "retains activity" is intended that the variant will have at least about 30%, at least about 50%, at least about 70%, or at least about 80% of the pesticidal activity of the native protein. Methods for measuring pesticidal activity are well known in the art. See, for example, Czapla and Lang (1990) *J. Econ. Entomol.* 83: 2480-2485; Andrews et al. (1988) *Biochem. J.* 252:199-206; Marrone et al. (1985) *J. of Economic Entomology* 78:290-293; and U.S. Pat. No. 5,743,477, all of which are herein incorporated by reference in their entirety.

The skilled artisan will further appreciate that changes can be introduced by mutation of the nucleotide sequences of the invention thereby leading to changes in the amino acid sequence of the encoded delta-endotoxin proteins, without altering the biological activity of the proteins. Thus, variant isolated nucleic acid molecules can be created by introducing one or more nucleotide substitutions, additions, or deletions into the corresponding nucleotide sequence disclosed herein, such that one or more amino acid substitutions, additions or deletions are introduced into the encoded protein. Mutations can be introduced by standard techniques, such as site-directed mutagenesis and PCR-mediated mutagenesis. Such variant nucleotide sequences are also encompassed by the present invention.

For example, conservative amino acid substitutions may be made at one or more predicted, nonessential amino acid residues. A "nonessential" amino acid residue is a residue that can be altered from the wild-type sequence of a delta-endotoxin protein without altering the biological activity, whereas an "essential" amino acid residue is required for biological activity. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Delta-endotoxins generally have five conserved sequence domains, and three conserved structural domains (see, for example, de Maagd et al. (2001) *Trends Genetics* 17:193-199). The first conserved structural domain consists of seven alpha helices and is involved in membrane insertion and pore formation. Domain II consists of three beta-sheets arranged in a Greek key configuration, and domain III consists of two antiparallel beta-sheets in "jelly-roll" formation (de Maagd et al., 2001, supra). Domains II and III are involved in receptor recognition and binding, and are therefore considered determinants of toxin specificity.

Conserved group 1 is found from about amino acid residue 174 to about 196 of SEQ ID NO:3. Conserved group 2 is found from about amino acid residue 250 to about 292 of SEQ ID NO:3. Conserved group 3 is found from about amino acid residue 476 to about 521 of SEQ ID NO:3. Conserved group 4 is found from about amino acid residue 542 to about 552 of SEQ ID NO:3. Conserved group 5 is found from about amino acid residue 618 to about 628 of SEQ ID NO:3.

Amino acid substitutions may be made in nonconserved regions that retain function. In general, such substitutions would not be made for conserved amino acid residues, or for amino acid residues residing within a conserved motif, where such residues are essential for protein activity. Examples of residues that are conserved and that may be essential for protein activity include, for example, residues that are identical between all proteins contained in an alignment of the amino acid sequences of the present invention and known delta-endotoxin sequences. Examples of residues that are conserved but that may allow conservative amino acid substitutions and still retain activity include, for example, residues that have only conservative substitutions between all proteins contained in an alignment of the amino acid sequences of the present invention and known delta-endotoxin sequences. However, one of skill in the art would understand that functional variants may have minor conserved or nonconserved alterations in the conserved residues.

Alternatively, variant nucleotide sequences can be made by introducing mutations randomly along all or part of the coding sequence, such as by saturation mutagenesis, and the resultant mutants can be screened for ability to confer delta-endotoxin activity to identify mutants that retain activity. Following mutagenesis, the encoded protein can be expressed recombinantly, and the activity of the protein can be determined using standard assay techniques.

Using methods such as PCR, hybridization, and the like corresponding delta-endotoxin sequences can be identified, such sequences having substantial identity to the sequences of the invention. See, for example, Sambrook and Russell (2001) *Molecular Cloning: A Laboratory Manual.* (Cold Spring Harbor Laboratory Press, Cold Spring Harbor, N.Y.) and Innis, et al. (1990) *PCR Protocols: A Guide to Methods and Applications* (Academic Press, NY).

In a hybridization method, all or part of the delta-endotoxin nucleotide sequence can be used to screen cDNA or genomic libraries. Methods for construction of such cDNA and genomic libraries are generally known in the art and are disclosed in Sambrook and Russell, 2001, supra. The so-called hybridization probes may be genomic DNA fragments, cDNA fragments, RNA fragments, or other oligonucleotides, and may be labeled with a detectable group such as $^{32}$P, or any other detectable marker, such as other radioisotopes, a fluorescent compound, an enzyme, or an enzyme co-factor. Probes for hybridization can be made by labeling synthetic oligonucleotides based on the known delta-endotoxin-encoding nucleotide sequence disclosed herein. Degenerate primers designed on the basis of conserved nucleotides or amino acid residues in the nucleotide sequence or encoded amino acid sequence can additionally be used. The probe typically comprises a region of nucleotide sequence that hybridizes under stringent conditions to at least about 12, at least about 25, at least about 50, 75, 100, 125, 150, 175, 200, 250, 300, 350, or 400 consecutive nucleotides of delta-endotoxin encoding nucleotide sequence of the invention or a fragment or variant thereof. Methods for the preparation of probes for hybridization are generally known in the art and are disclosed in Sambrook and Russell, 2001, supra herein incorporated by reference.

For example, an entire delta-endotoxin sequence disclosed herein, or one or more portions thereof, may be used as a probe capable of specifically hybridizing to corresponding delta-endotoxin-like sequences and messenger RNAs. To achieve specific hybridization under a variety of conditions, such probes include sequences that are unique and are preferably at least about 10 nucleotides in length, or at least about 20 nucleotides in length. Such probes may be used to amplify corresponding delta-endotoxin sequences from a chosen organism by PCR. This technique may be used to isolate additional coding sequences from a desired organism or as a diagnostic assay to determine the presence of coding sequences in an organism. Hybridization techniques include hybridization screening of plated DNA libraries (either plaques or colonies; see, for example, Sambrook et al. (1989)

*Molecular Cloning: A Laboratory Manual* (2d ed., Cold Spring Harbor Laboratory Press, Cold Spring Harbor, N.Y.).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Optionally, wash buffers may comprise about 0.1% to about 1% SDS. Duration of hybridization is generally less than about 24 hours, usually about 4 to about 12 hours.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem.* 138:267-284: $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≥90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, New York); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Cold Spring Harbor, N.Y.).

Isolated Proteins and Variants and Fragments Thereof

Delta-endotoxin proteins are also encompassed within the present invention. By "delta-endotoxin protein" is intended a protein having the amino acid sequence set forth in SEQ ID NO:9, 11, 13, 15, or 18. Fragments, biologically active portions, and variants thereof are also provided, and may be used to practice the methods of the present invention.

"Fragments" or "biologically active portions" include polypeptide fragments comprising amino acid sequences sufficiently identical to the amino acid sequence set forth in SEQ ID NO:9, 11, 13, 15, or 18, and that exhibit pesticidal activity (for example, SEQ ID NO:11, 13, and 15 are variants of SEQ ID NO:9). A biologically active portion of a delta-endotoxin protein can be a polypeptide that is, for example, 10, 25, 50, 100 or more amino acids in length. Such biologically active portions can be prepared by recombinant techniques and evaluated for pesticidal activity. Methods for measuring pesticidal activity are well known in the art. See, for example, Czapla and Lang (1990) *J. Econ. Entomol.* 83:2480-2485; Andrews et al. (1988) *Biochem. J.* 252:199-206; Marrone et al. (1985) *J. of Economic Entomology* 78:290-293; and U.S. Pat. No. 5,743,477, all of which are herein incorporated by reference in their entirety. As used here, a fragment comprises at least 8 contiguous amino acids of SEQ ID NO:9, 11, 13, 15, or 18. The invention encompasses other fragments, however, such as any fragment in the protein greater than about 10, 20, 30, 50, 100, 150, 200, 250, 300, 350, 400, 400, 450, 500, 550, or 600 amino acids.

By "variants" is intended proteins or polypeptides having an amino acid sequence that is at least about 60%, 65%, about 70%, 75%, about 80%, 85%, about 90%, 91%, 92%, 93%, 94%, 95%, 96%, 97%, 98% or 99% identical to the amino acid sequence of SEQ ID NO:9, 11, 13, 15, or 18. Variants also include polypeptides encoded by a nucleic acid molecule that hybridizes to the nucleic acid molecule of SEQ ID NO:1, 2, 4, 6, 7, 8, 10, 12, 14, 16, or 17, or a complement thereof, under stringent conditions. Variants include polypeptides that differ in amino acid sequence due to mutagenesis. Variant proteins encompassed by the present invention are biologically active; that is, they continue to possess the desired biological activity of the native protein that is retaining pesticidal activity. Methods for measuring pesticidal activity are well known in the art. See, for example, Czapla and Lang (1990) *J. Econ. Entomol.* 83:2480-2485; Andrews et al. (1988) *Biochem. J.* 252:199-206; Marrone et al. (1985) *J. of Economic Entomology* 78:290-293; and U.S. Pat. No. 5,743, 477, all of which are herein incorporated by reference in their entirety.

Bacterial genes, such as the genes of this invention, quite often possess multiple methionine initiation codons in proximity to the start of the open reading frame. Often, translation initiation at one or more of these start codons will lead to generation of a functional protein. For example, SEQ ID NO:9 (encoded by SEQ ID NO:6, 7, 8, and 16) represents a downstream start site of SEQ ID NO:5. These start codons can include ATG codons. However, bacteria such as *Bacillus* sp. also recognize the codon GTG as a start codon, and proteins that initiate translation at GTG codons contain a methionine at the first amino acid. Furthermore, it is not often determined a priori which of these codons are used naturally in the bacterium. Thus, it is understood that use of one of the alternate methionine codons may also lead to generation of delta-endotoxin proteins that encode pesticidal activity. These delta-endotoxin proteins are encompassed in the present invention and may be used in the methods of the present invention.

Antibodies to the polypeptides of the present invention, or to variants or fragments thereof, are also encompassed. Methods for producing antibodies are well known in the art (see, for example, Harlow and Lane (1988) *Antibodies: A Laboratory Manual*, Cold Spring Harbor Laboratory, Cold Spring Harbor, N.Y.; U.S. Pat. No. 4,196,265).

Altered or Improved Variants

It is recognized that DNA sequences of a delta-endotoxin may be altered by various methods, and that these alterations may result in DNA sequences encoding proteins with amino acid sequences different than that encoded by a delta-endotoxin of the present invention. This protein may be altered in various ways including amino acid substitutions, deletions, truncations, and insertions of one or more amino acids of SEQ ID NO:9, 11, 13, 15, or 18, including up to about 2, about 3, about 4, about 5, about 6, about 7, about 8, about 9, about 10, about 15, about 20, about 25, about 30, about 35, about 40, about 45, about 50, about 55, about 60, about 65, about 70, about 75, about 80, about 85, about 90, about 100, about 105, about 110, about 115, about 120, about 125, about 130 or more amino acid substitutions, deletions or insertions.

Methods for such manipulations are generally known in the art. For example, amino acid sequence variants of a delta-endotoxin protein can be prepared by mutations in the DNA. This may also be accomplished by one of several forms of mutagenesis and/or in directed evolution. In some aspects, the changes encoded in the amino acid sequence will not substantially affect the function of the protein. Such variants will possess the desired pesticidal activity. However, it is understood that the ability of a delta-endotoxin to confer pesticidal activity may be improved by the use of such techniques upon the compositions of this invention. For example, one may express a delta-endotoxin in host cells that exhibit high rates of base misincorporation during DNA replication, such as XL-1 Red (Stratagene). After propagation in such strains, one can isolate the delta-endotoxin DNA (for example by preparing plasmid DNA, or by amplifying by PCR and cloning the resulting PCR fragment into a vector), culture the delta-endotoxin mutations in a non-mutagenic strain, and identify mutated delta-endotoxin genes with pesticidal activity, for example by performing an assay to test for pesticidal activity. Generally, the protein is mixed and used in feeding assays. See, for example Marrone et al. (1985) *J. of Economic Entomology* 78:290-293. Such assays can include contacting plants with one or more pests and determining the plant's ability to survive and/or cause the death of the pests. Examples of mutations that result in increased toxicity are found in Schnepf et al. (1998) *Microbiol. Mol. Biol. Rev.* 62:775-806.

Alternatively, alterations may be made to the protein sequence of many proteins at the amino or carboxy terminus without substantially affecting activity. This can include insertions, deletions, or alterations introduced by modern molecular methods, such as PCR, including PCR amplifications that alter or extend the protein coding sequence by virtue of inclusion of amino acid encoding sequences in the oligonucleotides utilized in the PCR amplification. Alternatively, the protein sequences added can include entire protein-coding sequences, such as those used commonly in the art to generate protein fusions. Such fusion proteins are often used to (1) increase expression of a protein of interest (2) introduce a binding domain, enzymatic activity, or epitope to facilitate either protein purification, protein detection, or other experimental uses known in the art (3) target secretion or translation of a protein to a subcellular organelle, such as the periplasmic space of Gram-negative bacteria, or the endoplasmic reticulum of eukaryotic cells, the latter of which often results in glycosylation of the protein.

Variant nucleotide and amino acid sequences of the present invention also encompass sequences derived from mutagenic and recombinogenic procedures such as DNA shuffling. With such a procedure, one or more different delta-endotoxin protein coding regions can be used to create a new delta-endotoxin protein possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between a delta-endotoxin gene of the invention and other known delta-endotoxin genes to obtain a new gene coding for a protein with an improved property of interest, such as an increased insecticidal activity. Strategies for such DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458.

Domain swapping or shuffling is another mechanism for generating altered delta-endotoxin proteins. Domains II and III may be swapped between delta-endotoxin proteins, resulting in hybrid or chimeric toxins with improved pesticidal activity or target spectrum. Methods for generating recombinant proteins and testing them for pesticidal activity are well known in the art (see, for example, Naimov et al. (2001) *Appl. Environ. Microbiol.* 67:5328-5330; de Maagd et al. (1996) *Appl. Environ. Microbiol.* 62:1537-1543; Ge et al. (1991) *J. Biol. Chem.* 266:17954-17958; Schnepf et al. (1990) *J. Biol. Chem.* 265:20923-20930; Rang et al. 91999) *Appl. Environ. Microbiol.* 65:2918-2925).

Vectors

A delta-endotoxin sequence of the invention may be provided in an expression cassette for expression in a plant of interest. By "plant expression cassette" is intended a DNA construct that is capable of resulting in the expression of a protein from an open reading frame in a plant cell. Typically these contain a promoter and a coding sequence. Often, such constructs will also contain a 3' untranslated region. Such constructs may contain a "signal sequence" or "leader sequence" to facilitate co-translational or post-translational transport of the peptide to certain intracellular structures such as the chloroplast (or other plastid), endoplasmic reticulum, or Golgi apparatus.

By "signal sequence" is intended a sequence that is known or suspected to result in cotranslational or post-translational peptide transport across the cell membrane. In eukaryotes, this typically involves secretion into the Golgi apparatus, with some resulting glycosylation. By "leader sequence" is intended any sequence that when translated, results in an amino acid sequence sufficient to trigger co-translational transport of the peptide chain to a sub-cellular organelle. Thus, this includes leader sequences targeting transport and/or glycosylation by passage into the endoplasmic reticulum, passage to vacuoles, plastids including chloroplasts, mitochondria, and the like.

By "plant transformation vector" is intended a DNA molecule that is necessary for efficient transformation of a plant cell. Such a molecule may consist of one or more plant expression cassettes, and may be organized into more than one "vector" DNA molecule. For example, binary vectors are plant transformation vectors that utilize two non-contiguous DNA vectors to encode all requisite cis- and trans-acting functions for transformation of plant cells (Hellens and Mullineaux (2000) *Trends in Plant Science* 5:446-451). "Vector" refers to a nucleic acid construct designed for transfer between different host cells. "Expression vector" refers to a vector that has the ability to incorporate, integrate and express heterologous DNA sequences or fragments in a foreign cell. The cassette will include 5' and 3' regulatory sequences operably linked to a sequence of the invention. By "operably linked" is intended a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame. The cassette may additionally contain at least one additional gene to be cotransformed into the organism. Alternatively, the additional gene(s) can be provided on multiple expression cassettes.

"Promoter" refers to a nucleic acid sequence that functions to direct transcription of a downstream coding sequence. The promoter together with other transcriptional and translational regulatory nucleic acid sequences (also termed "control sequences") are necessary for the expression of a DNA sequence of interest.

Such an expression cassette is provided with a plurality of restriction sites for insertion of the delta-endotoxin sequence to be under the transcriptional regulation of the regulatory regions.

The expression cassette will include in the 5'-3' direction of transcription, a transcriptional and translational initiation region (i.e., a promoter), a DNA sequence of the invention, and a translational and transcriptional termination region (i.e., termination region) functional in plants. The promoter may be native or analogous, or foreign or heterologous, to the plant host and/or to the DNA sequence of the invention. Additionally, the promoter may be the natural sequence or alternatively a synthetic sequence. Where the promoter is "native" or "homologous" to the plant host, it is intended that the promoter is found in the native plant into which the promoter is introduced. Where the promoter is "foreign" or "heterologous" to the DNA sequence of the invention, it is intended that the promoter is not the native or naturally occurring promoter for the operably linked DNA sequence of the invention.

The termination region may be native with the transcriptional initiation region, may be native with the operably linked DNA sequence of interest, may be native with the plant host, or may be derived from another source (i.e., foreign or heterologous to the promoter, the DNA sequence of interest, the plant host, or any combination thereof). Convenient termination regions are available from the Ti-plasmid of *A. tumefaciens*, such as the octopine synthase and nopaline synthase termination regions. See also Guerineau et al. (1991) *Mol Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acid Res.* 15:9627-9639.

*Bacillus thuringiensis* genes have been found to be problematic when used for expression in higher plants. Expression from these native genes often leads to low accumulation of steady state mRNA and protein. This low accumulation has been shown to be due in part to ectopic splicing and/or polyadenylation of the nascent transcript by plant mRNA processing systems. Thus, several gene(s) of the invention have been optimized for increased expression in the transformed host cell.

Any of the nucleotide sequences described herein can be further optimized for expression in a host cell of interest. Thus, in one aspect of the invention, synthetic DNA sequences are designed for a given polypeptide, such as the polypeptides of the invention. Expression of the open reading frame of the synthetic DNA sequence in a cell results in production of the polypeptide of the invention. Synthetic DNA sequences can be useful to simply remove unwanted restriction endonuclease sites, to facilitate DNA cloning strategies, to alter or remove any potential codon bias, to alter or improve GC content, to remove or alter alternate reading frames, and/or to alter or remove intron/exon splice recognition sites, polyadenylation sites, Shine-Delgarno sequences, unwanted promoter elements and the like that may be present in a native DNA sequence. It is also possible that synthetic DNA sequences may be utilized to introduce other improvements to a DNA sequence, such as introduction of an intron sequence, creation of a DNA sequence that in expressed as a protein fusion to organelle targeting sequences, such as chloroplast transit peptides, apoplast/vacuolar targeting peptides, or peptide sequences that result in retention of the resulting peptide in the endoplasmic reticulum. Synthetic genes can also be synthesized using host cell-preferred codons for improved expression, or may be synthesized using codons at a host-preferred codon usage frequency. See, for example, Campbell and Gowri (1990) *Plant Physiol.* 92:1-11; U.S. Pat. Nos. 6,320,100; 6,075,185; 5,380,831; and 5,436,391, U.S. Published Application Nos. 20040005600 and 20010003849, and Murray et al. (1989) *Nucleic Acids Res.* 17:477-498, herein incorporated by reference.

The delta-endotoxin gene to be targeted to the chloroplast may be optimized for expression in the chloroplast to account for differences in codon usage between the plant nucleus and this organelle. In this manner, the nucleic acids of interest may be synthesized using chloroplast-preferred codons. See, for example, U.S. Pat. No. 5,380,831, herein incorporated by reference.

Plant Transformation

Methods of the invention involve introducing a nucleotide construct into a plant. By "introducing" is intended to present to the plant the nucleotide construct in such a manner that the construct gains access to the interior of a cell of the plant. The methods of the invention do not require that a particular method for introducing a nucleotide construct to a plant is used, only that the nucleotide construct gains access to the interior of at least one cell of the plant. Methods for introducing nucleotide constructs into plants are known in the art including, but not limited to, stable transformation methods, transient transformation methods, and virus-mediated methods.

By "plant" is intended whole plants, plant organs (e.g., leaves, stems, roots, etc.), seeds, plant cells, propagules, embryos and progeny of the same. Plant cells can be differentiated or undifferentiated (e.g. callus, suspension culture cells, protoplasts, leaf cells, root cells, phloem cells, pollen).

"Transgenic plants" or "transformed plants" or "stably transformed" plants or cells or tissues refers to plants that have incorporated or integrated exogenous nucleic acid sequences or DNA fragments into the plant cell. These nucleic acid sequences include those that are exogenous, or not present in the untransformed plant cell, as well as those that may be endogenous, or present in the untransformed plant cell. "Heterologous" generally refers to the nucleic acid sequences that are not endogenous to the cell or part of the native genome in which they are present, and have been added to the cell by infection, transfection, microinjection, electroporation, microprojection, or the like.

Transformation of plant cells can be accomplished by one of several techniques known in the art. The delta-endotoxin gene of the invention may be modified to obtain or enhance expression in plant cells. Typically a construct that expresses such a protein would contain a promoter to drive transcription of the gene, as well as a 3' untranslated region to allow transcription termination and polyadenylation. The organization of such constructs is well known in the art. In some instances, it may be useful to engineer the gene such that the resulting peptide is secreted, or otherwise targeted within the plant cell. For example, the gene can be engineered to contain a signal peptide to facilitate transfer of the peptide to the endoplasmic reticulum. It may also be preferable to engineer the plant expression cassette to contain an intron, such that mRNA processing of the intron is required for expression.

Typically this "plant expression cassette" will be inserted into a "plant transformation vector". This plant transformation vector may be comprised of one or more DNA vectors needed for achieving plant transformation. For example, it is a common practice in the art to utilize plant transformation vectors that are comprised of more than one contiguous DNA segment. These vectors are often referred to in the art as "binary vectors". Binary vectors as well as vectors with helper plasmids are most often used for *Agrobacterium*-mediated transformation, where the size and complexity of DNA segments needed to achieve efficient transformation is quite large, and it is advantageous to separate functions onto separate DNA molecules. Binary vectors typically contain a plasmid vector that contains the cis-acting sequences required for T-DNA transfer (such as left border and right border), a selectable marker that is engineered to be capable of expression in a plant cell, and a "gene of interest" (a gene engineered to be capable of expression in a plant cell for which generation of transgenic plants is desired). Also present on this plasmid vector are sequences required for bacterial replication. The cis-acting sequences are arranged in a fashion to allow efficient transfer into plant cells and expression therein. For example, the selectable marker gene and the delta-endotoxin are located between the left and right borders. Often a second plasmid vector contains the trans-acting factors that mediate T-DNA transfer from *Agrobacterium* to plant cells. This plasmid often contains the virulence functions (Vir genes) that allow infection of plant cells by *Agrobacterium*, and transfer of DNA by cleavage at border sequences and vir-mediated DNA transfer, as is understood in the art (Hellens and Mullineaux (2000) *Trends in Plant Science* 5:446-451). Several types of *Agrobacterium* strains (e.g. LBA4404, GV3101, EHA101, EHA105, etc.) can be used for plant transformation. The second plasmid vector is not necessary for transforming the plants by other methods such as microprojection, microinjection, electroporation, polyethylene glycol, etc.

In general, plant transformation methods involve transferring heterologous DNA into target plant cells (e.g. immature or mature embryos, suspension cultures, undifferentiated callus, protoplasts, etc.), followed by applying a maximum threshold level of appropriate selection (depending on the selectable marker gene) to recover the transformed plant cells from a group of untransformed cell mass. Explants are typically transferred to a fresh supply of the same medium and cultured routinely. Subsequently, the transformed cells are differentiated into shoots after placing on regeneration medium supplemented with a maximum threshold level of selecting agent. The shoots are then transferred to a selective rooting medium for recovering rooted shoot or plantlet. The transgenic plantlet then grows into a mature plant and produces fertile seeds (e.g. Hiei et al. (1994) *The Plant Journal* 6:271-282; Ishida et al. (1996) *Nature Biotechnology* 14:745-750). Explants are typically transferred to a fresh supply of the same medium and cultured routinely. A general description of the techniques and methods for generating transgenic plants are found in Ayres and Park (1994) *Critical Reviews in Plant Science* 13:219-239 and Bommineni and Jauhar (1997) *Maydica* 42:107-120. Since the transformed material contains many cells; both transformed and non-transformed cells are present in any piece of subjected target callus or tissue or group of cells. The ability to kill non-transformed cells and allow transformed cells to proliferate results in transformed plant cultures. Often, the ability to remove non-transformed cells is a limitation to rapid recovery of transformed plant cells and successful generation of transgenic plants.

Transformation protocols as well as protocols for introducing nucleotide sequences into plants may vary depending on the type of plant or plant cell, i.e., monocot or dicot, targeted for transformation. Generation of transgenic plants may be performed by one of several methods, including, but not limited to, microinjection, electroporation, direct gene transfer, introduction of heterologous DNA by *Agrobacterium* into plant cells (*Agrobacterium*-mediated transformation), bombardment of plant cells with heterologous foreign DNA adhered to particles, ballistic particle acceleration, aerosol beam transformation (U.S. Published Application No. 20010026941; U.S. Pat. No. 4,945,050; International Publication No. WO 91/00915; U.S. Published Application No. 2002015066), Lec1 transformation, and various other non-particle direct-mediated methods to transfer DNA.

Methods for transformation of chloroplasts are known in the art. See, for example, Svab et al. (1990) *Proc. Natl. Acad. Sci. USA* 87:8526-8530; Svab and Maliga (1993) *Proc. Natl. Acad. Sci. USA* 90:913-917; Svab and Maliga (1993) *EMBO J.* 12:601-606. The method relies on particle gun delivery of DNA containing a selectable marker and targeting of the DNA to the plastid genome through homologous recombination. Additionally, plastid transformation can be accomplished by transactivation of a silent plastid-borne transgene by tissue-preferred expression of a nuclear-encoded and plastid-directed RNA polymerase. Such a system has been reported in McBride et al. (1994) *Proc. Natl. Acad. Sci. USA* 91:7301-7305.

Following integration of heterologous foreign DNA into plant cells, one then applies a maximum threshold level of appropriate selection in the medium to kill the untransformed cells and separate and proliferate the putatively transformed cells that survive from this selection treatment by transferring regularly to a fresh medium. By continuous passage and challenge with appropriate selection, one identifies and proliferates the cells that are transformed with the plasmid vector. Molecular and biochemical methods can then be used to confirm the presence of the integrated heterologous gene of interest into the genome of the transgenic plant.

The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting hybrid having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present invention provides transformed seed (also referred to as "transgenic seed") having a nucleotide construct of the invention, for example, an expression cassette of the invention, stably incorporated into their genome.

Evaluation of Plant Transformation

Following introduction of heterologous foreign DNA into plant cells, the transformation or integration of heterologous gene in the plant genome is confirmed by various methods such as analysis of nucleic acids, proteins and metabolites associated with the integrated gene.

PCR analysis is a rapid method to screen transformed cells, tissue or shoots for the presence of incorporated gene at the earlier stage before transplanting into the soil (Sambrook and Russell (2001) *Molecular Cloning: A Laboratory Manual*. Cold Spring Harbor Laboratory Press, Cold Spring Harbor, N.Y.). PCR is carried out using oligonucleotide primers specific to the gene of interest or *Agrobacterium* vector background, etc.

Plant transformation may be confirmed by Southern blot analysis of genomic DNA (Sambrook and Russell, 2001, supra). In general, total DNA is extracted from the transformant, digested with appropriate restriction enzymes, fractionated in an agarose gel and transferred to a nitrocellulose or nylon membrane. The membrane or "blot" is then probed with, for example, radiolabeled $^{32}P$ target DNA fragment to confirm the integration of introduced gene into the plant genome according to standard techniques (Sambrook and Russell, 2001, supra).

In Northern blot analysis, RNA is isolated from specific tissues of transformant, fractionated in a formaldehyde agarose gel, and blotted onto a nylon filter according to standard procedures that are routinely used in the art (Sambrook and Russell, 2001, supra). Expression of RNA encoded by the delta-endotoxin is then tested by hybridizing the filter to a radioactive probe derived from a delta-endotoxin, by methods known in the art (Sambrook and Russell, 2001, supra).

Western blot, biochemical assays and the like may be carried out on the transgenic plants to confirm the presence of protein encoded by the delta-endotoxin gene by standard procedures (Sambrook and Russell, 2001, supra) using antibodies that bind to one or more epitopes present on the delta-endotoxin protein.

Pesticidal Activity in Plants

In another aspect of the invention, one may generate transgenic plants expressing a delta-endotoxin that has pesticidal activity. Methods described above by way of example may be utilized to generate transgenic plants, but the manner in which the transgenic plant cells are generated is not critical to this invention. Methods known or described in the art such as *Agrobacterium*-mediated transformation, biolistic transformation, and non-particle-mediated methods may be used at the discretion of the experimenter. Plants expressing a delta-endotoxin may be isolated by common methods described in the art, for example by transformation of callus, selection of transformed callus, and regeneration of fertile plants from such transgenic callus. In such process, one may use any gene as a selectable marker so long as its expression in plant cells confers ability to identify or select for transformed cells.

A number of markers have been developed for use with plant cells, such as resistance to chloramphenicol, the aminoglycoside G418, hygromycin, or the like. Other genes that encode a product involved in chloroplast metabolism may also be used as selectable markers. For example, genes that provide resistance to plant herbicides such as glyphosate, bromoxynil, or imidazolinone may find particular use. Such genes have been reported (Stalker et al. (1985) *J. Biol. Chem.* 263:6310-6314 (bromoxynil resistance nitrilase gene); and Sathasivan et al. (1990) *Nucl. Acids Res.* 18:2188 (AHAS imidazolinone resistance gene). Additionally, the genes disclosed herein are useful as markers to assess transformation of bacterial or plant cells. Methods for detecting the presence of a transgene in a plant, plant organ (e.g., leaves, stems, roots, etc.), seed, plant cell, propagule, embryo or progeny of the same are well known in the art. In one embodiment, the presence of the transgene is detected by testing for pesticidal activity.

Fertile plants expressing a delta-endotoxin may be tested for pesticidal activity, and the plants showing optimal activity selected for further breeding. Methods are available in the art to assay for pest activity. Generally, the protein is mixed and used in feeding assays. See, for example Marrone et al. (1985) *J. of Economic Entomology* 78:290-293.

The present invention may be used for transformation of any plant species, including, but not limited to, monocots and dicots. Examples of plants of interest include, but are not limited to, corn (maize), sorghum, wheat, sunflower, tomato, crucifers, peppers, potato, cotton, rice, soybean, sugarbeet, sugarcane, tobacco, barley, and oilseed rape, *Brassica* sp., alfalfa, rye, millet, safflower, peanuts, sweet potato, cassava, coffee, coconut, pineapple, citrus trees, cocoa, tea, banana, avocado, fig, guava, mango, olive, papaya, cashew, macadamia, almond, oats, vegetables, ornamentals, and conifers.

Vegetables include, but are not limited to, tomatoes, lettuce, green beans, lima beans, peas, and members of the genus *Curcumis* such as cucumber, cantaloupe, and musk melon. Ornamentals include, but are not limited to, azalea, hydrangea, hibiscus, roses, tulips, daffodils, petunias, carnation, poinsettia, and chrysanthemum. Preferably, plants of the present invention are crop plants (for example, maize, sorghum, wheat, sunflower, tomato, crucifers, peppers, potato, cotton, rice, soybean, sugarbeet, sugarcane, tobacco, barley, oilseed rape, etc.).

Use in Pest Control

General methods for employing strains comprising a nucleotide sequence of the present invention, or a variant thereof, in pesticide control or in engineering other organisms as pesticidal agents are known in the art. See, for example U.S. Pat. No. 5,039,523 and EP 0480762A2.

The *Bacillus* strains containing a nucleotide sequence of the present invention, or a variant thereof, or the microorganisms that have been genetically altered to contain a pesticidal gene and protein may be used for protecting agricultural crops and products from pests. In one aspect of the invention, whole, i.e., unlysed, cells of a toxin (pesticide)-producing organism are treated with reagents that prolong the activity of the toxin produced in the cell when the cell is applied to the environment of target pest(s).

Alternatively, the pesticide is produced by introducing a delta-endotoxin gene into a cellular host. Expression of the delta-endotoxin gene results, directly or indirectly, in the intracellular production and maintenance of the pesticide. In one aspect of this invention, these cells are then treated under conditions that prolong the activity of the toxin produced in the cell when the cell is applied to the environment of target pest(s). The resulting product retains the toxicity of the toxin. These naturally encapsulated pesticides may then be formulated in accordance with conventional techniques for application to the environment hosting a target pest, e.g., soil, water, and foliage of plants. See, for example EPA 0192319, and the references cited therein. Alternatively, one may formulate the cells expressing a gene of this invention such as to allow application of the resulting material as a pesticide.

Pesticidal Compositions

The active ingredients of the present invention are normally applied in the form of compositions and can be applied to the crop area or plant to be treated, simultaneously or in succession, with other compounds. These compounds can be fertilizers, weed killers, cryoprotectants, surfactants, detergents, pesticidal soaps, dormant oils, polymers, and/or time-release or biodegradable carrier formulations that permit long-term dosing of a target area following a single application of the formulation. They can also be selective herbicides, chemical insecticides, virucides, microbicides, amoebicides, pesticides, fungicides, bacteriocides, nematocides, molluscicides or mixtures of several of these preparations, if desired, together with further agriculturally acceptable carriers, surfactants or application-promoting adjuvants customarily employed in the art of formulation. Suitable carriers and adjuvants can be solid or liquid and correspond to the substances ordinarily employed in formulation technology, e.g. natural or regenerated mineral substances, solvents, dispersants, wetting agents, tackifiers, binders or fertilizers. Likewise the formulations may be prepared into edible "baits" or fashioned into pest "traps" to permit feeding or ingestion by a target pest of the pesticidal formulation.

Methods of applying an active ingredient of the present invention or an agrochemical composition of the present invention that contains at least one of the pesticidal proteins produced by the bacterial strains of the present invention include leaf application, seed coating and soil application. The number of applications and the rate of application depend on the intensity of infestation by the corresponding pest.

The composition may be formulated as a powder, dust, pellet, granule, spray, emulsion, colloid, solution, or such like, and may be prepared by such conventional means as desiccation, lyophilization, homogenation, extraction, filtration, centrifugation, sedimentation, or concentration of a culture of cells comprising the polypeptide. In all such compositions that contain at least one such pesticidal polypeptide, the polypeptide may be present in a concentration of from about 1% to about 99% by weight.

Lepidopteran or coleopteran pests may be killed or reduced in numbers in a given area by the methods of the invention, or may be prophylactically applied to an environmental area to prevent infestation by a susceptible pest. Preferably the pest ingests, or is contacted with, a pesticidally-effective amount of the polypeptide. By "pesticidally-effective amount" is intended an amount of the pesticide that is able to bring about death to at least one pest, or to noticeably reduce pest growth, feeding, or normal physiological development. This amount will vary depending on such factors as, for example, the specific target pests to be controlled, the specific environment, location, plant, crop, or agricultural site to be treated, the environmental conditions, and the method, rate, concentration, stability, and quantity of application of the pesticidally-effective polypeptide composition. The formulations may also vary with respect to climatic conditions, environmental considerations, and/or frequency of application and/or severity of pest infestation.

The pesticide compositions described may be made by formulating either the bacterial cell, crystal and/or spore suspension, or isolated protein component with the desired agriculturally-acceptable carrier. The compositions may be formulated prior to administration in an appropriate means such as lyophilized, freeze-dried, desiccated, or in an aqueous carrier, medium or suitable diluent, such as saline or other buffer. The formulated compositions may be in the form of a dust or granular material, or a suspension in oil (vegetable or mineral), or water or oil/water emulsions, or as a wettable powder, or in combination with any other carrier material suitable for agricultural application. Suitable agricultural carriers can be solid or liquid and are well known in the art. The term "agriculturally-acceptable carrier" covers all adjuvants, inert components, dispersants, surfactants, tackifiers, binders, etc. that are ordinarily used in pesticide formulation technology; these are well known to those skilled in pesticide formulation. The formulations may be mixed with one or more solid or liquid adjuvants and prepared by various means, e.g., by homogeneously mixing, blending and/or grinding the pesticidal composition with suitable adjuvants using conventional formulation techniques. Suitable formulations and application methods are described in U.S. Pat. No. 6,468,523, herein incorporated by reference.

"Pest" includes but is not limited to, insects, fungi, bacteria, nematodes, mites, ticks, and the like. Insect pests include insects selected from the orders Coleoptera, Diptera, Hymenoptera, Lepidoptera, Mallophaga, Homoptera, Hemiptera, Orthroptera, Thysanoptera, Dermaptera, Isoptera, Anoplura, Siphonaptera, Trichoptera, etc., particularly Coleoptera, Lepidoptera, and Diptera.

The order Coleoptera includes the suborders Adephaga and Polyphaga. Suborder Adephaga includes the superfamilies Caraboidea and Gyrinoidea, while suborder Polyphaga includes the superfamilies Hydrophiloidea, Staphylinoidea, Cantharoidea, Cleroidea, Elateroidea, Dascilloidea, Dryopoidea, Byrrhoidea, Cucujoidea, Meloidea, Mordelloidea, Tenebrionoidea, Bostrichoidea, Scarabaeoidea, Cerambycoidea, Chrysomeloidea, and Curculionoidea. Superfamily Caraboidea includes the families Cicindelidae, Carabidae, and Dytiscidae. Superfamily Gyrinoidea includes the family Gyrinidae. Superfamily Hydrophiloidea includes the family Hydrophilidae. Superfamily Staphylinoidea includes the families Silphidae and Staphylinidae. Superfamily Cantharoidea includes the families Cantharidae and Lampyridae. Superfamily Cleroidea includes the families Cleridae and Dermestidae. Superfamily Elateroidea includes the families Elateridae and Buprestidae. Superfamily Cucujoidea includes the family Coccinellidae. Superfamily Meloidea includes the family Meloidae. Superfamily Tenebrionoidea includes the family Tenebrionidae. Superfamily Scarabaeoidea includes the families Passalidae and Scarabaeidae. Superfamily Cerambycoidea includes the family Cerambycidae. Superfamily Chrysomeloidea includes the family Chrysomelidae. Superfamily Curculionoidea includes the families Curculionidae and Scolytidae.

The order Diptera includes the Suborders Nematocera, Brachycera, and Cyclorrhapha. Suborder Nematocera includes the families Tipulidae, Psychodidae, Culicidae, Ceratopogonidae, Chironomidae, Simuliidae, Bibionidae, and Cecidomyiidae. Suborder Brachycera includes the families Stratiomyidae, Tabanidae, Therevidae, Asilidae, Mydidae, Bombyliidae, and Dolichopodidae. Suborder Cyclorrhapha includes the Divisions Aschiza and Aschiza. Division Aschiza includes the families Phoridae, Syrphidae, and Conopidae. Division Aschiza includes the Sections Acalyptratae and Calyptratae. Section Acalyptratae includes the families Otitidae, Tephritidae, Agromyzidae, and Drosophilidae. Section Calyptratae includes the families Hippoboscidae, Oestridae, Tachinidae, Anthomyiidae, Muscidae, Calliphoridae, and Sarcophagidae.

The order Lepidoptera includes the families Papilionidae, Pieridae, Lycaenidae, Nymphalidae, Danaidae, Satyridae, Hesperiidae, Sphingidae, Saturniidae, Geometridae, Arctiidae, Noctuidae, Lymantriidae, Sesiidae, and Tineidae.

Insect pests of the invention for the major crops include: Maize: *Ostrinia nubilalis*, European corn borer; *Agrotis ipsilon*, black cutworm; *Helicoverpa zea*, corn earworm; *Spodoptera frugiperda*, fall armyworm; *Diatraea grandiosella*, southwestern corn borer; *Elasmopalpus lignosellus*, lesser cornstalk borer; *Diatraea saccharalis*, surgarcane borer; *Diabrotica virgifera*, western corn rootworm; *Diabrotica longicornis barberi*, northern corn rootworm; *Diabrotica undecimpunctata howardi*, southern corn rootworm; *Melanotus* spp., wireworms; *Cyclocephala borealis*, northern masked chafer (white grub); *Cyclocephala immaculata*, southern masked chafer (white grub); *Popillia japonica*, Japanese beetle; *Chaetocnema pulicaria*, corn flea beetle; *Sphenophorus maidis*, maize billbug; *Rhopalosiphum maidis*, corn leaf aphid; *Anuraphis maidiradicis*, corn root aphid; *Blissus leucopterus leucopterus*, chinch bug; *Melanoplus femurrubrum*, redlegged grasshopper; *Melanoplus sanguinipes*, migratory grasshopper; *Hylemya platura*, seedcorn maggot; *Agromyza parvicornis*, corn blot leafminer; *Anaphothrips obscrurus*, grass thrips; *Solenopsis milesta*, thief ant; *Tetranychus urticae*, twospotted spider mite; Sorghum: *Chilo partellus*, sorghum borer; *Spodoptera frugiperda*, fall armyworm; *Helicoverpa zea*, corn earworm; *Elasmopalpus lignosellus*, lesser cornstalk borer; *Feltia subterranea*, granulate cutworm; *Phyllophaga crinita*, white grub; *Eleodes, Conoderus*, and *Aeolus* spp., wireworms; *Oulema melanopus*, cereal leaf beetle; *Chaetocnema pulicaria*, corn flea beetle; *Sphenophorus maidis*, maize billbug; *Rhopalosiphum maidis*; corn leaf aphid; *Sipha flava*, yellow sugarcane aphid; *Blissus leucopterus leucopterus*, chinch bug; *Contarinia sorghicola*, sorghum midge; *Tetranychus cinnabarinus*, carmine spider mite; *Tetranychus urticae*, twospotted spider mite; Wheat: *Pseudaletia unipunctata*, army worm; *Spodoptera frugiperda*, fall armyworm; *Elasmopalpus lignosellus*, lesser cornstalk borer; *Agrotis orthogonia*, western cutworm; *Elasmopalpus lignosellus*, lesser cornstalk borer; *Oulema melanopus*, cereal leaf beetle; *Hypera punctata*, clover leaf weevil; *Diabrotica undecimpunctata howardi*, southern corn rootworm; Russian wheat aphid; *Schizaphis graminum*, greenbug; *Macrosiphum avenae*, English grain aphid; *Melanoplus femurrubrum*, redlegged grasshopper; *Melanoplus differentialis*, differential grasshopper; *Melanoplus sanguinipes*, migratory grasshopper; *Mayetiola destructor*, Hessian fly; *Sitodiplosis mosellana*, wheat midge; *Meromyza americana*, wheat stem maggot; Hylemya coarctata, wheat bulb fly; *Frankliniella fusca*, tobacco thrips; *Cephus cinctus*, wheat stem sawfly; *Aceria tulipae*, wheat curl mite; Sunflower: *Suleima helianthana*, sunflower bud moth; *Homoeosoma electellum*, sunflower moth; zygogramma exclamationis, sunflower beetle; *Bothyrus gibbosus*, carrot beetle; *Neolasioptera murtfeldtiana*, sunflower seed midge; Cotton: *Heliothis virescens*, cotton budworm; *Helicoverpa zea*, cotton bollworm; *Spodoptera exigua*, beet armyworm; *Pectinophora gossypiella*, pink bollworm; *Anthonomus grandis*, boll weevil; *Aphis gossypii*, cotton aphid; *Pseudatomoscelis seriatus*, cotton fleahopper; *Trialeurodes abutilonea*, bandedwinged whitefly; *Lygus lineolaris*, tarnished plant bug; *Melanoplus femurrubrum*, redlegged grasshopper; *Melanoplus differentialis*, differential grasshopper; *Thrips tabaci*, onion thrips; *Frankliniella fusca*, tobacco thrips; *Tetranychus cinnabarinus*, carmine spider mite; *Tetranychus urticae*, twospotted spider mite; Rice: *Diatraea saccharalis*, sugarcane borer; *Spodoptera frugiperda*, fall armyworm; *Helicoverpa zea*, corn earworm; *Colaspis brunnea*, grape colaspis; *Lissorhoptrus oryzophilus*, rice water weevil; *Sitophilus oryzae*, rice weevil; *Nephotettix nigropictus*, rice leafhopper; *Blissus leucopterus leucopterus*, chinch bug; *Acrosternum hilare*, green stink bug; Soybean: *Pseudoplusia includens*, soybean looper; *Anticarsia gemmatalis*, velvetbean caterpillar; *Plathypena scabra*, green cloverworm; *Ostrinia nubilalis*, European corn borer; *Agrotis ipsilon*, black cutworm; *Spodoptera exigua*, beet armyworm; *Heliothis virescens*, cotton budworm; *Helicoverpa zea*, cotton bollworm; *Epilachna varivestis*, Mexican bean beetle; *Myzus persicae*, green peach aphid; *Empoasca fabae*, potato leafhopper; *Acrosternum hilare*, green stink bug; *Melanoplus femurrubrum*, redlegged grasshopper; *Melanoplus differentialis*, differential grasshopper; *Hylemya platura*, seedcorn maggot; *Sericothrips variabilis*, soybean thrips; *Thrips tabaci*, onion thrips; *Tetranychus turkestani*, strawberry spider mite; *Tetranychus urticae*, twospotted spider mite; Barley: *Ostrinia nubilalis*, European corn borer; *Agrotis ipsilon*, black cutworm; *Schizaphis graminum*, greenbug; *Blissus leucopterus leucopterus*, chinch bug; *Acrosternum hilare*, green stink bug; *Euschistus servus*, brown stink bug; *Delia platura*, seedcorn maggot; *Mayetiola destructor*, Hessian fly; *Petrobia latens*, brown wheat mite; Oil Seed Rape: *Brevicoryne brassicae*, cabbage aphid; *Phyllotreta cruciferae*, Flea beetle; *Mamestra configurata*, Bertha armyworm; *Plutella xylostella*, Diamond-back moth; *Delia* ssp., Root maggots.

Nematodes include parasitic nematodes such as root-knot, cyst, and lesion nematodes, including *Heterodera* spp., *Meloidogyne* spp., and *Globodera* spp.; particularly members of the cyst nematodes, including, but not limited to, *Heterodera glycines* (soybean cyst nematode); *Heterodera schachtii* (beet cyst nematode); *Heterodera avenae* (cereal cyst nematode); and *Globodera rostochiensis* and *Globodera pailida* (potato cyst nematodes). Lesion nematodes include *Pratylenchus* spp.

Methods for Increasing Plant Yield

Methods for increasing plant yield are provided. The methods comprise introducing into a plant or plant cell a polynucleotide comprising a pesticidal sequence disclosed herein. As defined herein, the "yield" of the plant refers to the quality and/or quantity of biomass produced by the plant. By "biomass" is intended any measured plant product. An increase in biomass production is any improvement in the yield of the measured plant product. Increasing plant yield has several commercial applications. For example, increasing plant leaf biomass may increase the yield of leafy vegetables for human or animal consumption. Additionally, increasing leaf biomass can be used to increase production of plant-derived pharmaceutical or industrial products. An increase in yield can comprise any statistically significant increase including, but not limited to, at least a 1% increase, at least a 3% increase, at least a 5% increase, at least a 10% increase, at least a 20% increase, at least a 30%, at least a 50%, at least a 70%, at least a 100% or a greater increase in yield compared to a plant not expressing the pesticidal sequence.

In specific methods, plant yield is increased as a result of improved pest resistance of a plant expressing a pesticidal protein disclosed herein. Expression of the pesticidal protein results in a reduced ability of a pest to infest or feed on the plant, thus improving plant yield.

The following examples are offered by way of illustration and not by way of limitation.

EXPERIMENTAL

Example 1

Generation of Synthetic and Variant Genes

In one aspect of the invention, synthetic axmi-004 sequences were generated, for example synaxmi-004 (SEQ ID NO:1) and synaxmi-004B (SEQ ID NO:2). These synthetic sequences have an altered DNA sequence relative to the axmi-004 sequence (SEQ ID NO:3) recited in U.S. patent application Ser. No. 10/782,020, herein incorporated by reference), and encode the original AXMI-004 protein. Likewise, synaxmi-004B-2M (SEQ ID NO:4) was designed and encodes the axmi-004 alternate start site (herein referred to as axmi-004B-2M and set forth in SEQ ID NO:5) originally identified in U.S. patent application Ser. No. 10/782,020.

In another aspect of the invention, a third start site was identified in the axmi-004 coding sequence. This coding region is designated axmi-004B-3M (SEQ ID NO:16) and encodes the AXMI-004B-3M amino acid sequence set forth in SEQ ID NO:9. Synthetic sequences encoding the AXMI-004B-3M protein were also designed. These synthetic nucleotide sequences were designated synaxmi-004B-3M, synaxmi-004C-3M, and synaxmi-004D-3M and are set forth in SEQ ID NO:6, 7, and 8, respectively.

In another aspect of the invention, modified versions of the nucleotide sequence encoding AXMI-004B-3M protein were designed such that additional N-terminal residues are added to the encoded protein. These sequence are designated synaxmi-004B-3M-alt1 (SEQ ID NO:10), synaxmi-004B-3M-alt2 (SEQ ID NO:12), synaxmi-004B-3M-alt3 (SEQ ID NO:14), and synaxmi-004B-3M-alt4 (SEQ ID NO:17). The encoded proteins are designated AXMI-004B-3M-ALT1 (SEQ ID NO:11), AXMI-004B-3M-ALT2 (SEQ ID NO:13), AXMI-004B-3M-ALT3 (SEQ ID NO:15), and AXMI-004B-3M-ALT4 (SEQ ID NO:18).

Example 2

Vectoring of the Pesticidal Genes of the Invention for Plant Expression

Each of the coding regions of the genes of the invention are connected independently with appropriate promoter and terminator sequences for expression in plants. Such sequences are well known in the art and may include the rice actin promoter or maize ubiquitin promoter for expression in monocots, the *Arabidopsis* UBQ3 promoter or CaMV 35S promoter for expression in dicots, and the nos or PinII terminators. Techniques for producing and confirming promoter—gene—terminator constructs also are well known in the art.

Select sequences (Table 1) were expressed in a bacterial host cell and were found to have pesticidal activity against Lepidopteran species.

TABLE 1

Vectoring of synthetic and variant sequences

| Gene Name | Nucleotide SEQ ID NO: | Amino acid SEQ ID NO: | Clone Designation |
|---|---|---|---|
| synaxmi-004B-2M | 4 | 5 | pAX3252 |
| synaxmi-004B-3M | 6 | 9 | pAX4538 |
| synaxmi-004C-3M | 7 | 9 | pAX3141 |
| synaxmi-004D-3M | 8 | 9 | pAX3142 |
| synaxmi-004B-3m-alt1 | 10 | 11 | pAX4522 |
|  |  |  | pAX4515 |
| synaxmi-004B-3M-alt2 | 12 | 13 | pAX4517 |
| synaxmi-004B-3M-alt3 | 14 | 15 | pAX4518 |

Example 3

Assays for Pesticidal Activity

The ability of a pesticidal protein to act as a pesticide upon a pest is often assessed in a number of ways. One way well known in the art is to perform a feeding assay. In such a feeding assay, one exposes the pest to a sample containing either compounds to be tested, or control samples. Often this is performed by placing the material to be tested, or a suitable dilution of such material, onto a material that the pest will ingest, such as an artificial diet. The material to be tested may be composed of a liquid, solid, or slurry. The material to be tested may be placed upon the surface and then allowed to dry. Alternatively, the material to be tested may be mixed with a molten artificial diet, then dispensed into the assay chamber. The assay chamber may be, for example, a cup, a dish, or a well of a microtiter plate.

Assays for sucking pests (for example aphids) may involve separating the test material from the insect by a partition, ideally a portion that can be pierced by the sucking mouthparts of the sucking insect, to allow ingestion of the test material. Often the test material is mixed with a feeding stimulant, such as sucrose, to promote ingestion of the test compound.

Other types of assays can include microinjection of the test material into the mouth, or gut of the pest, as well as development of transgenic plants, followed by test of the ability of the pest to feed upon the transgenic plant. Plant testing may involve isolation of the plant parts normally consumed, for example, small cages attached to a leaf, or isolation of entire plants in cages containing insects.

Other methods and approaches to assay pests are known in the art, and can be found, for example in Robertson, J. L. & H. K. Preisler. 1992. *Pesticide bioassays with arthropods*. CRC, Boca Raton, Fla. Alternatively, assays are commonly described in the journals "Arthropod Management Tests" and "Journal of Economic Entomology" or by discussion with members of the Entomological Society of America (ESA).

Example 4

Transformation of the Genes of the Invention into Plant Cells by *Agrobacterium*-Mediated Transformation Ears are collected 8-12 days after pollination. Embryos are isolated from the ears, and those embryos 0.8-1.5 mm in size are used for transformation. Embryos are plated scutellum side-up on a suitable incubation media, and incubated overnight at 25° C. in the dark. However, it is not necessary per se to incubate the embryos overnight. Embryos are contacted with an *Agrobacterium* strain containing the appropriate vectors for Ti plasmid mediated transfer for 5-10 min, and then plated onto co-cultivation media for 3 days (25° C. in the dark). After co-cultivation, explants are transferred to recovery period media for five days (at 25° C. in the dark). Explants are incubated in selection media for up to eight weeks, depending on the nature and characteristics of the particular selection utilized. After the selection period, the resulting callus is transferred to embryo maturation media, until the formation of mature somatic embryos is observed. The resulting mature somatic embryos are then placed under low light, and the process of regeneration is initiated as known in the art. The resulting shoots are allowed to root on rooting media, and the resulting plants are transferred to nursery pots and propagated as transgenic plants.

Example 5

Transformation of Maize Cells with the Pesticidal Genes of the Invention

Maize ears are collected 8-12 days after pollination. Embryos are isolated from the ears, and those embryos 0.8-1.5 mm in size are used for transformation. Embryos are plated scutellum side-up on a suitable incubation media, such as DN62A5S media (3.98 g/L N6 Salts; 1 mL/L (of 1000× Stock) N6 Vitamins; 800 mg/L L-Asparagine; 100 mg/L Myo-inositol; 1.4 g/L L-Proline; 100 mg/L Casaminoacids; 50 g/L sucrose; 1 mL/L (of 1 mg/mL Stock) 2,4-D), and incubated overnight at 25° C. in the dark.

The resulting explants are transferred to mesh squares (30-40 per plate), transferred onto osmotic media for 30-45 minutes, then transferred to a beaming plate (see, for example, PCT Publication No. WO/0138514 and U.S. Pat. No. 5,240, 842).

DNA constructs designed to express the genes of the invention in plant cells are accelerated into plant tissue using an aerosol beam accelerator, using conditions essentially as described in PCT Publication No. WO/0138514. After beaming, embryos are incubated for 30 min on osmotic media, then placed onto incubation media overnight at 25° C. in the dark. To avoid unduly damaging beamed explants, they are incubated for at least 24 hours prior to transfer to recovery media. Embryos are then spread onto recovery period media, for 5 days, 25° C. in the dark, then transferred to a selection media. Explants are incubated in selection media for up to eight weeks, depending on the nature and characteristics of the particular selection utilized. After the selection period, the resulting callus is transferred to embryo maturation media, until the formation of mature somatic embryos is observed. The resulting mature somatic embryos are then placed under low light, and the process of regeneration is initiated by methods known in the art. The resulting shoots are allowed to root on rooting media, and the resulting plants are transferred to nursery pots and propagated as transgenic plants.

Materials

| DN62A5S Media | | |
|---|---|---|
| Components | per liter | Source |
| Chu'S N6 Basal Salt Mixture (Prod. No. C 416) | 3.98 g/L | Phytotechnology Labs |
| Chu's N6 Vitamin Solution (Prod. No. C 149) | 1 mL/L (of 1000x Stock) | Phytotechnology Labs |
| L-Asparagine | 800 mg/L | Phytotechnology Labs |
| Myo-inositol | 100 mg/L | Sigma |
| L-Proline | 1.4 g/L | Phytotechnology Labs |
| Casaminoacids | 100 mg/L | Fisher Scientific |
| Sucrose | 50 g/L | Phytotechnology Labs |
| 2, 4-D (Prod. No. D-7299) | 1 mL/L (of 1 mg/mL Stock) | Sigma |

Adjust the pH of the solution to pH to 5.8 with 1N KOH/1N KCl, add Gelrite (Sigma) to 3 g/L, and autoclave. After cooling to 50° C., add 2 ml/L of a 5 mg/ml stock solution of Silver Nitrate (Phytotechnology Labs). Recipe yields about 20 plates.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. An isolated polypeptide with pesticidal activity, selected from the group consisting of:
   a) a polypeptide comprising the amino acid sequence of SEQ ID NO:11, 13, 15, or 18;
   b) a polypeptide that is encoded by the nucleotide sequence of SEQ ID NO:10, 12, 14, or 17.

2. The polypeptide of claim 1 further comprising heterologous amino acid sequences.

3. A composition comprising the polypeptide of claim 1.

4. The composition of claim 3, wherein said composition is selected from the group consisting of a powder, dust, pellet, granule, spray, emulsion, colloid, and solution.

5. The composition of claim 3, wherein said composition is prepared by desiccation, lyophilization, homogenization, extraction, filtration, centrifugation, sedimentation, or concentration of a culture of *Bacillus thuringiensis* cells.

6. The composition of claim 3, comprising from about 1% to about 99% by weight of said polypeptide.

7. A method for controlling a lepidopteran or coleopteran pest population comprising contacting said population with a pesticidally-effective amount of the polypeptide of claim 1.

8. A method for killing a lepidopteran or coleopteran pest, comprising contacting said pest with, or feeding to said pest, a pesticidally-effective amount of the polypeptide of claim 1.

* * * * *